US008669253B2

(12) United States Patent
Rao et al.

(10) Patent No.: US 8,669,253 B2
(45) Date of Patent: Mar. 11, 2014

(54) METHODS FOR TREATING GLAUCOMA AND MACULAR DEGENERATION

(75) Inventors: Vasantha P. Rao, Cary, NC (US);
Patrick J. Casey, Chapel Hill, NC (US);
Peifeng Deng, Chapel Hill, NC (US);
Yuri K. Peterson, Durham, NC (US)

(73) Assignee: Duke University, Durham, NC (US)

( * ) Notice: Subject to any disclaimer, the term of this patent is extended or adjusted under 35 U.S.C. 154(b) by 1007 days.

(21) Appl. No.: 11/716,724

(22) Filed: Mar. 12, 2007

(65) Prior Publication Data

US 2007/0249010 A1     Oct. 25, 2007

Related U.S. Application Data

(60) Provisional application No. 60/781,730, filed on Mar. 14, 2006.

(51) Int. Cl.
*A61K 31/41*     (2006.01)
*A61K 31/53*     (2006.01)

(52) U.S. Cl.
USPC .......................... 514/241; 514/359; 514/913

(58) Field of Classification Search
USPC ........................................ 514/241, 359, 913
See application file for complete search history.

(56) References Cited

U.S. PATENT DOCUMENTS

| | | | | |
|---|---|---|---|---|
| 2002/0006967 | A1* | 1/2002 | Campochiaro | 514/715 |
| 2004/0116425 | A1* | 6/2004 | Li et al. | 514/241 |
| 2006/0004032 | A1* | 1/2006 | Zheng et al. | 514/275 |

OTHER PUBLICATIONS

Rao et al.; "Effects of Pharmacologic Inhibition of Protein Geranylgeranyltransferase Type I on Aqueous Humor Outflow through the Trabecular Meshwork"; Investigative Ophthalmology & Visual Science; Jun. 2008; vol. 49; No. 6; pp. 2464-2471.
Meyer-Ter-Vehn et al.; "Lovastatin Inhibits TGF-[beta]-Induced Myofibroblast Transdifferentiation in Human Tenon Fibroblasts"; Investigative Ophthalmology & Visual Science; Sep. 2008; vol. 49; No. 9; pp. 3955-3960.
Zhang et al; "Blebbistatin, a Novel Inhibitor of Myosin II ATPase Activity, Increases Aqueous Humor Outflow Facility in Perfused Enucleated Porcine Eyes"; Investigative Ophthalmology & Visual Science; Nov. 2005; vol. 46; No. 11; pp. 4130-4138.
Rao et al.; "Modulation of Aqueous Humor Outflow Facility by the Rho Kinase-Specific Inhibitor Y-27632"; Investigative Ophthalmology & Visual Science; Apr. 2001; vol. 42; No. 5; pp. 1029-1037.
Peterson et al.; "A Novel Protein Geranylgeranyltransferase-I Inhibitor with High Potency, Selectivity, and Cellular Activity"; Journal of Biological Chemistry; May 5, 2006; vol. 281; No. 18; pp. 12445-12450.
Song et al; "Effects of Cholesterol-Lowering Statins on the Aqueous Humor Outflow Pathway"; Investigative Ophthalmology & Visual Science; Jul. 2005; vol. 46; No. 7; pp. 2424-2432.
Zhang et al; "Novel molecular insights into RhoA GTPase-induced resistance to aqueous humor outflow through the trabecular meshwork"; American Journal of Physiology Cell Physiology; Nov. 2008; vol. 295; No. 5; pp. C1057-C1070.
Deng et al.; "Pharmacological Inhibition of Protein Geranylgeranyltransferase Type I (GGTase-I) by GGTI-DU40 Increase Aqueous Humor Outflow in Perfused Porcine Eyes"; Pharmacological Intervention and Cellular Mechanisms I; Program Number/Board # Range: 431-B89; Apr. 30, 2006; available on-line in advance of meeting.
James E. Sidaway et al., "Inhibitors of 3-Hydroxy-3-Methylglutaryl-CoA Reductase Reduce Receptor-Mediated Endocytosis in Opossum Kidney Cells," J. Am Soc Nephrol 2004; 15;2258-2265.
J.-Y. Pille et al., "Anti-RhoA and Anti-RhoC siRNAs Inhibit the Proliferation and Invasiveness of MDA-MB-231 Breast Cancer Cells in Vitro and in Vivo," Molecular Therapy, Feb. 2005, vol. 11, No. 2, pp. 267-274.
Hans E. Huber et al., "Anions Modulate the Potency of Geranylgeranyl-Protein Transferase I Inhibitors," The Journal of Biological Chemistry, Jul. 6, 2001, vol. 276, No. 27, pp. 24457-24465.
Robert B. Lobell et al., "Evaluation of Farnesyl:Protein Transferase and Geranylgeranyl:Protein Transferase Inhibitor Combinations in Preclinical Models," Cancer Research, Dec. 15, 2001, 61, pp. 8758-8768.
N. R. Veillard et al., "Simvastatin Modulates Chemokine and Chemokine Receptor Expression by Geranylgeranyl Isoprenoid Pathway in Human Endothelial Cells and Macrophages," Atherosclerosis, Nov. 28, 2005 (Abstract only).
E. T. Efuet et al., "Farnesyl and Geranylgeranyl Transferase Inhibitors Induce g1 Arrest by Targeting the Proteasome," Cancer Res. Jan. 15, 2006; 66(2):1040-51 (Abstract only).
G. McGwin Jr., et al., "Statins and Other Cholesterol-Loweirng Mdications and the Presenece of Galucoma," Arch Ophthalmol. Jun. 2004; 122(6):822-6 (Abstract only).
J. Song et al., "Effects of Cholesterol-Lowering Statins on the Aqueous Humor Outlow Pathway," Invest Ophthalmol Vis Sci. Jul. 2005;46(7):2424-32 (Abstract only).
A. F. Tilkin-Mariame et al., "Geranylgeranyl Transferase Inhibition Stimulates Anti-Melanoma Immune Response Through MHC Class I and Costimulatory Molecule Expression," FASEB J. Sep. 2005;19(11):1513-5 (Abstract only).
Department of Chemistry, "Cancer Chemotherapy: New, Selective Anhydride Inhibitors of Geranylgeranyl-Protein Transferase," http://www.chem.ucl.ac.uk/people/marson/newpages/research2.html; pp. 1-5.
Rodrigo Santucci, MD et al., "Farnesyltransferase Inhibitors of Their Role in the Treatment of Multiple Myeloma," Cancer Control, Sep./Oct. 2003, vol. 10, No. 5, pp. 384-387.
Fraser P. Coxon et al., "Identification of a Novel Phosphonocarboxylate Inhibitor of Rab Geranylgeranyl Transferase That Scpecifically Prevents Rab Prenylation in Osteoclasts and Macrophages," The Journal of Biological Chemistry, Dec. 21, 2001; vol. 276, No. 18, pages 48213-48222.
"Other Inhibitors: Inhibitors of FTase, GGTase, & Methyltransferase," pp. 1-4, http://www.emdbiosciences.com/html/CBC/other_inhibitors_FTase_and_GGTase.htm.

* cited by examiner

*Primary Examiner* — Zohreh Fay
(74) *Attorney, Agent, or Firm* — Banner & Witcoff, Ltd.

(57) ABSTRACT

Inhibition of geranylgeranylation of Rho GTPases and heterotrimeric G-proteins in the aqueous outflow pathway increases aqueous humor outflow, possibly through the tissue relaxation, and through altered cell adhesive interactions and actin cytoskeletal organization in cells of the outflow pathway. In addition, such inhibition is useful for treating age-related macular degeneration. The GGTase-I enzyme is a molecular target for lowering increased ocular pressure in glaucoma patients.

26 Claims, 11 Drawing Sheets

Figure 6A-6B
Fig. 6A
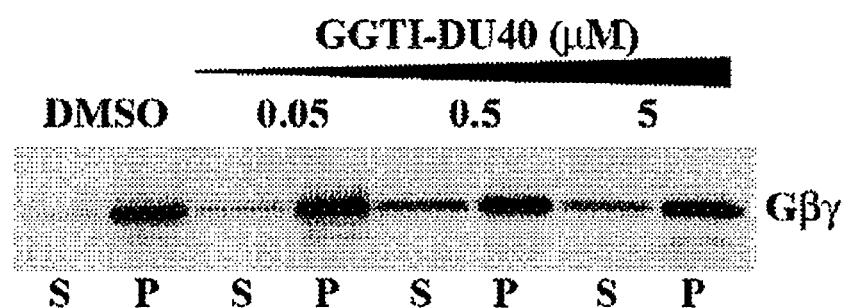
Fig. 6B
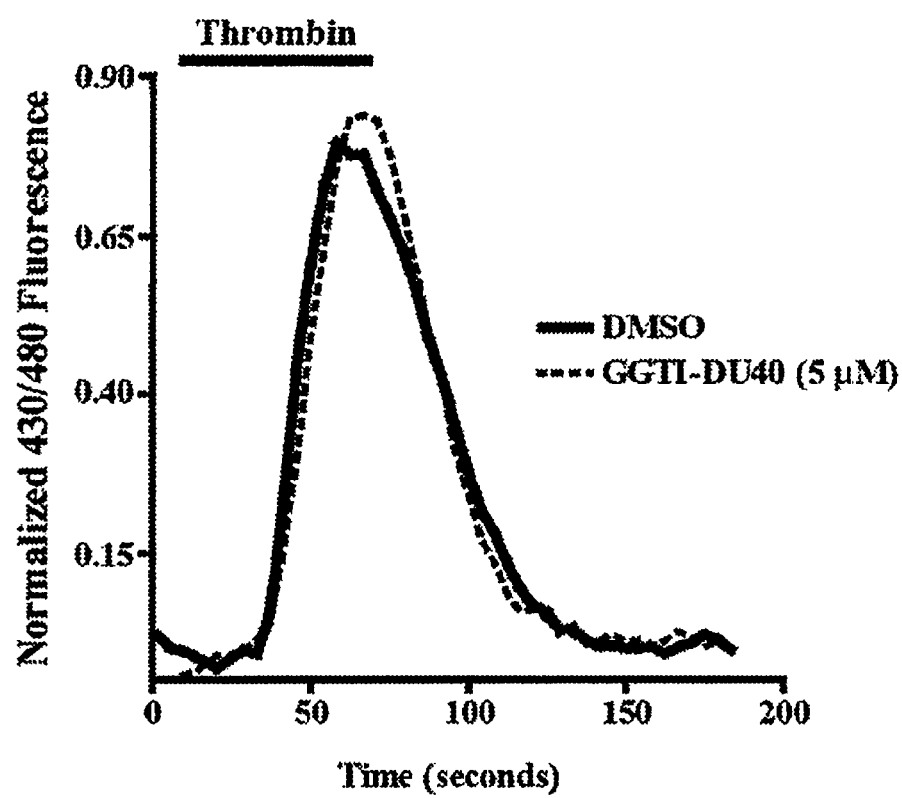

METHODS FOR TREATING GLAUCOMA AND MACULAR DEGENERATION

This application is a non-provisional of provisional Application Ser. No. 60/781,730 filed Mar. 14, 2006, the disclosure of which is expressly incorporated herein.

The invention was made using funds from the United States government under grants R01 EY013573 and R01 GM46372, both from the National Institutes of Health. The government retains certain rights under the terms of those grants.

TECHNICAL FIELD OF THE INVENTION

This invention is related to the area of eye diseases. In particular, it relates to treating diseases such as glaucoma and macular degeneration

BACKGROUND OF THE INVENTION

A promising strategy for the development of anti-cancer drugs is to suppress activation of oncogenic proteins such as Ras superfamily members. Functional Ras proteins require the addition of an isoprenoid lipid via a process directed by a C-terminal sequence termed the CaaX motif (1, 2), in which a cysteine (C) residue is followed by a dipeptide (aa) that is usually aliphatic and a variable residue (X) that dictates the prenyl group added. An X residue of Ser, Met, Gln, Cys, or Ala directs addition of the 15-carbon farnesyl lipid, while a Leu residue can direct modification by the 20-carbon geranylgeranyl isoprenoid (3). Following addition of the isoprenoid, most CaaX proteins are further processed by the Rcel protease, which removes the -aaX residues, and isoprenylcysteine carboxymethyltranferase (Icmt) to yield a protein containing a C-terminal isoprenylcysteine carboxymethylester (4).

The CaaX prenyltranferases protein farnesyltransferase (FTase) and protein geranylgeranyltransferase type I (GGTase-I)(5) add either a 15 carbon farnesyl group or a 20 carbon geranylgeranyl group, respectively, to the cysteine found within the CaaX motif. The prenyltransferase holoenzyme consists of an alpha subunit that is shared between the two forms of enzymes and a distinct beta subunit that binds substrates and thereby also confers prenyl group specificity (1). FTase substrates include Ras GTPases, nuclear lamins, several protein kinases and phosphatases, as well as other regulatory proteins (5). GGTase-I substrates include Rac and Rho GTPases and the gamma subunits of most heterotrimeric G-proteins (6). A structural bioinformatics analysis of the human genome has indicated that roughly 130 proteins are modified by the two enzymes, with substrates being divided nearly equally between FTase and GGTase (3).

The realization that many CaaX proteins, most notably Ras family members, are involved in pathologies such as cancer, inflammation and viral infectivity (4, 7, 8, 9), has spurred efforts to develop inhibitors of CaaX processing as a rational approach to therapeutic development. The major effort in this regard has been development of FTase inhibitors termed FTIs. FTIs developed rapidly from early CaaX peptide mimics (10) into the small organic ligands that have now shown efficacy in clinical trials, particularly hematologic and breast cancers (11, 12). FTI development was unusually rapid as multiple groups developed structurally distinct drugs that all demonstrated similar biological/pharmacological properties in preclinical models and unambiguously indicated that drug action was due principally to inhibition of FTase. These results however, have been overshadowed by unexpected clinical shortcomings, particularly against solid tumors (13, 14). One postulated explanation for this clinical limitation is the increased geranylgeranylation of protein such as K-Ras when FTase activity is inhibited, a processes referred to as alternate prenylation (15, 16, 17).

The discovery of alternate prenylation, coupled with the increasing evidence for involvement of geranylgeranylated proteins in pathological processes such as cancer, inflammation, and viral infectivity has led to increased interest in therapeutic targeting of GGTase-I. Although development of FTIs has garnered considerably more interest than that of GGTIs, several peptidomimetic GGTIs have been described. These include aminobenzoic acid derivatives such as GGTI-298 and GGTI-2154 (18, 19) and benzoyleneurea-based compounds (20). Studies with these compounds have revealed a number of consequences of cellular exposure to a GGTI. Administration of GGTI to cells can cause cell cycle arrest at G0/G1, and this effect appears to be mediated by inactivation of CDK2/4 through the p21/p15 kinase inhibitors downstream of Rho (21, 22). GGTIs are also potent stimulators of apoptosis in both normal (23, 24) and transformed cell lines (25, 26).

The complex nature of CaaX protein localization and function leaves multiple points where disregulation can occur, and therefore multiple points for therapeutic intervention are possible. Although the efficacy of prenyltransferase inhibitors in treating cancer is now considered quite genuine, if still against a limited number of cancers, the rational application of protein prenyltransferase inhibitors is growing more complex as the roles for multiple GTPases and other CaaX containing proteins are elucidated.

Glaucoma is a leading cause of blindness. It is a progressive optic neuropathy often caused by elevated intracoular pressure (IOP) consequent to abnormally high resistance to aqueous humor drainage via trabecular meshwork (T.M.) and Schlemm's canal (SC). The conventional route of aqueous humor outflow through T.M. and SC is generally thought to be the major pathway for the drainage of aqueous humor from the eye. Although there exist various medications to lower intraocular pressure in glaucoma patients, there is no specific drug which selectively targets the TM pathway.

Age-related macular degeneration (AMD) causes progressive impairment of central vision and is the leading cause of irreversible vision loss in older Americans. The most severe form of AMD involves neovascular/exudative (wet) and/or atrophic (dry) changes to the macula. Although the etiology of AMD remains largely unknown, implicated risk factors include age, ethnicity, smoking, hypertension, obesity and diet. Extracellular protein/lipid deposits (drusen) between the basal lamina of the retinal pigment epithelium (RPE) and the inner layer of Bruchs' membrane are associated with an increased risk of progressing to an advanced form of AMD, either geographic atrophy or exudative disease. The presence of large and indistinct (soft) drusen coupled with RPE abnormalities is considered an early form of the disorder and is often referred to as age-related maculopathy (ARM).

There is a continuing need in the art to develop drug treatments for alleviating the symptoms of glaucoma and age-related macular degeneration.

SUMMARY OF THE INVENTION

One embodiment of the invention provides a method of treating glaucoma in a patient. A selective inhibitor of geranylgeranyl transferase is administered to the patient. Aqueous humor outflow through the trabecular meshwork pathway is thereby increased.

Another embodiment of the invention provides a method of identifying candidate drugs for treatment of glaucoma. An inhibitor of geranylgeranyl transferase I is tested to determine its effect on myosin light chain phosphorylation in trabecular mesh cells. An inhibitor of geranylgeranyl transferase I which decreases the phosphorylation is identified as a candidate drug for treating glaucoma.

Yet another embodiment of the invention provides a method of identifying candidate drugs for treatment of glaucoma. An inhibitor of geranylgeranyl transferase I is tested to determine its effect on aqueous humor outflow in perfused cultured organs or organ segments. An inhibitor of geranylgeranyl transferase I which increases said outflow is identified as a candidate drug for treating glaucoma.

A further embodiment of the invention provides a method of identifying candidate drugs for treatment of glaucoma. An inhibitor of geranylgeranyl transferase I is tested to determine its effect on intraocular pressure in an experimental animal, wherein an inhibitor of geranylgeranyl transferase I which decreases said pressure is identified as a candidate drug for treating glaucoma.

Another aspect of the present invention is an ophthalmic solution comprising a selective inhibitor of geranylgeranyl transferase I and an ophthalmically acceptable carrier.

An additional embodiment of the invention is a method of treating age-related macular degeneration (ARM) in a patient. An effective dose of a selective inhibitor of geranylgeranyl transferase I is administered to the patient. Macular degeneration is thereby slowed or halted.

These and other embodiments which will be apparent to those of skill in the art upon reading the specification provide the art with new tools, methods and reagents for treating glaucoma and age-related macular degeneration.

BRIEF DESCRIPTION OF THE DRAWINGS

FIG. 1A. Molecular structure of GGTI-DU40 ($C_{30}H_{31}Cl_2N_5O_3S$ FW=612.58) and SN-DU40. FIG. 1B. Imapct of GGTI-DU40 on the enzymatic activity of GGTase-I (■), GGTase-II (□), FTase (▼), and Icmt (○). Enzymatic activity of GGTase-I in the presence of SN-DU40 is also shown (Δ). Data represent the mean and standard deviation of four measurements from two independent experiments.

FIGS. 2C and 2D are double-reciprocal plots of data from panels A and B, respectively. GGTI-DU40 concentrations used are: no drug (■, DMSO only), or 2 nM (○), 5 nM (Δ), 10 nM (▼), or 20 nM (◇) GGTI-DU40. Data represent the mean of duplicate determinations from a single experiment. Similar results were obtained in 3 independent experiments for each condition.

FIG. 4A-4B. GGTI-DU40 treatment inhibits Rap1 geranylgeranylation. Whole cell lysates from cells treated with GGTI-DU40 or vehicle for 24 h were harvested and processed for immunoblot analysis using an antisera specific for the unprenylated form of Rap1a (FIG. 4A). The blot was then stripped and reprobed with an antisera recognizing total Rap1 (FIG. 4B). The immunoblots presented are representative of four independent experiments for each condition. FIG. 4C. GGTI-DU40 treatment blocks Rho association with RhoGDI. Whole cell lysates from cells treated with GGTI-DU40 (5 μM), FTI L-744,832 (20 μM) or vehicle as in FIG. 4A-4B were incubated with GST-RhoGDI or GST alone, following which bound proteins were isolated using glutathione sepharose. Samples, including the input cell lysates (representing 50% of that used in the pull-down) were then processed for immunoblot analysis using Rho-specific antisera. The immunoblot presented is representative of more than four independent experiments.

FIG. 6A-6B. Effects of GGTI-DU40 treatment on membrane on Gβγ processing and inhibit thrombin-stimulated calcium flux. FIG. 6A. Impact of GGTI-DU40 treatment on Gβγ processing. MDA-MB-231 cells were treated with either vehicle or the indicated concentration of GGTI-DU40 for 24 h, following which lysates were prepared and fractionated by centrifugation at 100,000×g for 45 min. The resulting pellet (P) and supernatant (S) fractions were processed for immunoblotting with antisera against Gβ. The immunoblots presented are from the same experiment which is representative of five independent experiments. FIG. 6B. Impact of GGTI-DU40 treatment on thrombin-stimulated calcium flux. MDA-MB-231 cells were treated with either vehicle or GGTI-DU40 (5 μM) for 24 h subsequent to Fura-2 AM loading and thrombin stimulation as described in "Materials and Methods". The ratio of Fura-2 fluorescence (excitation at 340 or 380 nm and emission at 510 nm) was monitored during superfusion of thrombin. Integration of time with fluorescence to calculate total calcium flux confirmed no statistical difference between control and GGTI-DU40 treated samples. Data shown are from a single experiment and are representative of 4 such experiments.

DETAILED DESCRIPTION OF THE INVENTION

Figure 1A:
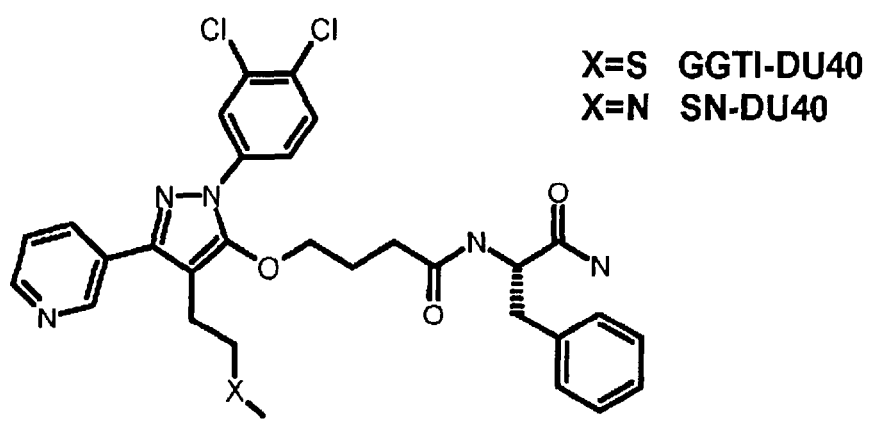
FIG. 1A-1B. GGTI-DU40 is a high potency inhibitor of GGTase-I.

The inventors have discovered that GGTase-I inhibitors, particularly those of a particular class, have biological effects on eyes that are beneficial, for example, in the treatment of glaucoma and/or age-related macular degeneration. Importantly, the aqueous humor outflow was increased from eyes that had been treated with GGTase-I inhibitors. In addition, they caused decreases in actin stress fibers and focal adhesions. Moreover, myosin light chain phosphorylation was decreased significantly and membrane localization of Rho, Rap, and G-beta/gamma was impaired in treated trabecular meshwork cells.

Many inhibitors of GGTase-I are known in the art, and any of these can be used. See for example Marson, et al., (*Bioorg. Med. Chem. Lett.* 12: 255-259, 2002) which discloses cyclic acid anhydrides as selective non-peptidic inhibitors. See also Sebti and Hamilton, *Esp. Opin. Invest. Drugs,* 9:2767-2782, 2000, and Sebti and Hamilton, *Current Opinion in Oncology,* 9:557-561, 1997. See also U.S. Patent Application Publication No. US 2004/0116425. The disclosures of these references are expressly incorporated herein. Any of such inhibitors can be tested according to the invention and used.

Examples of GGTI-1 inhibitors known in the art are:

| Compound Name | Compound Structure | R = | Reference No. |
|---|---|---|---|
| GGTI-286 | 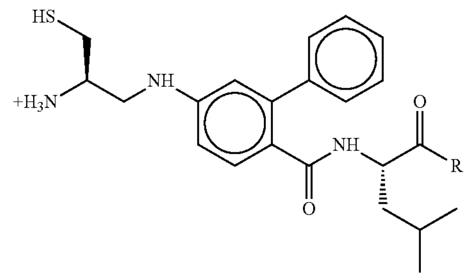 | $OCH_3$ | 18 |
| GGTI-287 | 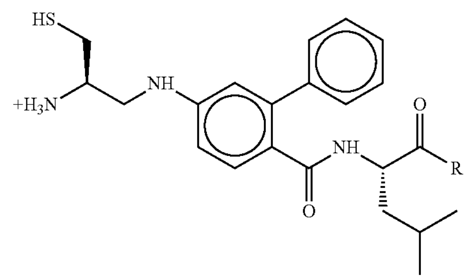 | $O^-$ | 18 |
| GGTI-297 | 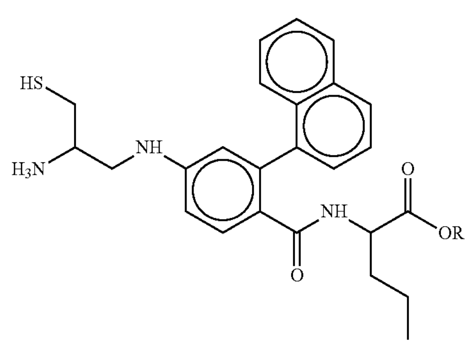 | H | 6 |

-continued

| Compound Name | Compound Structure | R = | Reference No. |
|---|---|---|---|
| GGTI-298 | 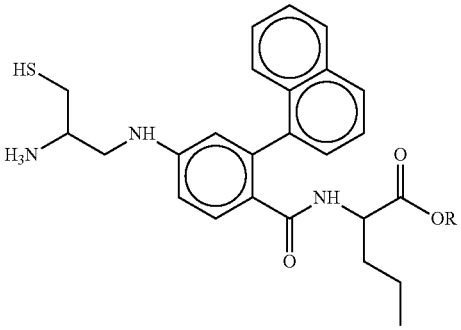 | CH₃ | 6 |
| GGTI-2133 | 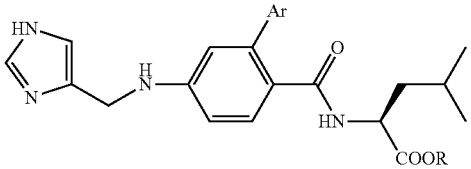 | H, and Ar = 1-naphthyl | 19 |
| GGTI-2147 | 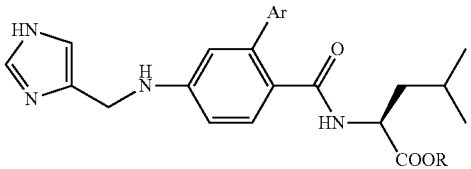 | CH₃, and Ar = 1-naphthyl | 19 |
| GGTI-2166 | 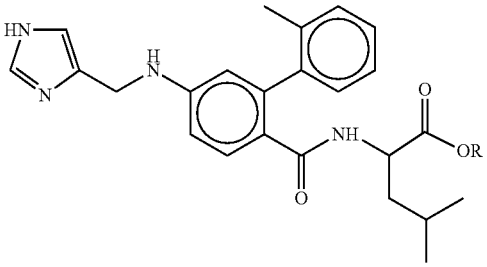 | CH₃ | 6 |

A particularly preferred class of compounds according to the invention are of the formula:

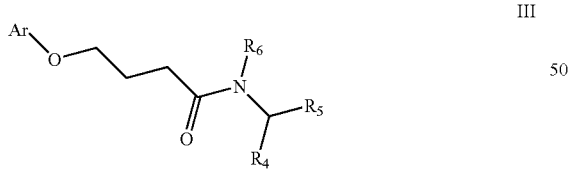

III wherein Ar is

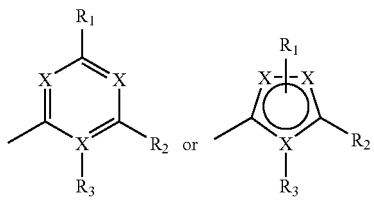

each X is independently C, N, O or S;

$R_1$ is phenyl, benzyl, methyl, ethyl, propyl, pyrimidine, 3,4-dimethylphenyl, 3-chloropyridazine, 2,4-dimethylpyrimidine, 3,4-difluorophenyl, 3,4-dichlorophenyl, 3,5-dichlorophenyl, $CH_2CF_3$, 4-trifluoromethylphenyl, 4-nitrophenyl, 4-bromophenyl, 3-bromophenyl, 4-methylphenyl, 4-methoxyphenyl, 4-chloro-2-methylphenyl, 4-fluorophenyl, 4-sulfonamidophenyl, 3-methoxyphenyl, 4-chlorophenyl, 3-chlorophenyl, 3,5-difluorophenyl, 4-aminophenyl, 1,3-dimethylpyrazole, ethanol, or 3,4-methylenedioxyphenyl;

$R_2$ is methyl, pyridine, pyridine-1-oxide, 3-cyanophenyl, 3-aminophenyl, 3-amidinophenyl, 3-dimethylaminophenyl, 2-methylthiazole, 4-methylthiadiazole, thiadiazole, 5-methylisoxazole, pyrazine, pyrimidine, 5-methylimidazole, 5-methylpyrazole, 2-benzylsulfanylpyridine, 6-benzylsulfanylpyridine, $CH_2COOH$, $N(CH_3)_2$, $CH_2CH_2SCH_3$ or $CH_2$-piperidinyl;

$R_3$ is absent, H, $CH_2CH_2OH$, $CH_2CH_2OCH_3$, $CH_2CH_2N(CH_3)_2$, $CH_2CH_2NHCH_3$, $CH_2OH$, $(CH_2)_3OH$, $CH_2CH_2CO_2H$, $CH_2CO_2H$, $CH_2CH_2SOCH_3$, $CH_2CH_2SO_2CH_3$, $CH_2CH_2SH$ or $CH_2CH_2SCH_3$;

$R_4$ is absent, H, $NH_2$, $CON(CH_3)_2$, $CO_2H$, $CN$, $CH_2OH$, $CONH_2$, $CSNH_2$, $CONHOH$, $C(NH)NH_2$, $CONHNH_2$, $CONHCH_3$, $CH_2OCH_3$, $CONH$-cyclohexyl, $CO_2CH_3$,

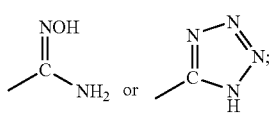

$R_5$ is absent, isopropyl, benzyl, 4-trifluoromethylbenzyl, 4-cyanobenzyl, 4-benzoylbenzyl, 3-chlorobenzyl, pentafluorobenzyl, 3,4-dichlorobenzyl, 2-fluorobenzyl, 4-methoxybenzyl, $CH_2CH_2$-phenyl, 4-fluorobenzyl, 4-phenylbenzyl, $CH_2$-imidazole, $CH_2COOH$, $CH_2CH_2COOH$, $(CH_2)_4NH_2$, $CH_2CH_2SCH_3$, 4-hydroxybenzyl, $CH_2$-naphthyl, 4-methylbenzyl, $CH_2$-indole, $CH_2$-thiophene, $CH_2$-cyclohexane, 4-chlorobenzyl, phenyl, $_2$-hydroxybenzyl, 4-tertbutoxybenzyl, $CH_2$-benzylimidazole, 4-aminobenzyl, $CH_2$-pryid-3-yl, $CH_2$-pryid-2-yl, $CH_2OH$, $(CH_2)_3NHC(NH)NH_2$ or $CH_2CH(CH_3)_2$; and, $R_6$ is H, methyl, ethyl, propyl, isopropyl, $CH_2CO_2H$, $CH_2CO_2Et$, benzyl, or $CH_2$-(2-methoxynaphthyl); or, $R_5$ and $R_6$ together form:

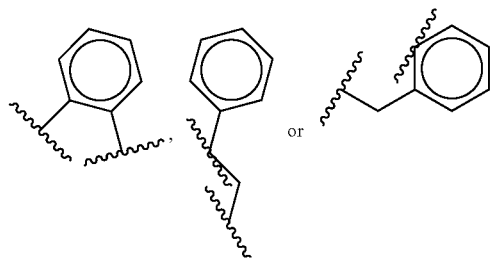

The methods and formulations can employ either crystalline and non-crystalline (e.g., amorphous) forms of the salts of the compounds. These salts can be used to increase the solubility or stability of the compounds disclosed herein. They may also aid in the isolation and purification of the compounds.

"Alkyl" groups according to the present invention are aliphatic hydrocarbons which can be straight, branched or cyclic. Alkyl groups optionally can be substituted with one or more substituents, such as a halogen, alkenyl, alkynyl, aryl, hydroxy, amino, thio, alkoxy, carboxy, oxo or cycloalkyl. There may be optionally inserted along the alkyl group one or more oxygen, sulfur or substituted or unsubstituted nitrogen atoms. Exemplary alkyl groups include methyl, ethyl, propyl, i-propyl, n-butyl, t-butyl, bicycloheptane (norbornane), cyclobutane, dimethyl-cyclobutane, cyclopentane, cyclohexane, fluoromethyl, difluoromethyl, trifluoromethyl, chloromethyl, trichloromethyl, and pentafluoroethyl. Preferably, alkyl groups have from about 1 to about 20 carbon atom chains, more preferably from about 1 to about 10 carbon atoms, still more preferably from about 1 to about 6 carbon atoms, and most preferably from about 1 to about 4 carbon atoms.

"Aryl" groups are monocyclic or bicyclic carbocyclic or heterocyclic aromatic ring moieties. Aryl groups can be substituted with one or more substituents, such as a halogen, alkenyl, alkyl, alkynyl, hydroxy, amino, thio, alkoxy or cycloalkyl.

"Heteroaryl" refers to monocyclic or bicyclic aromatic ring having at least one heteroatom selected from nitrogen, sulfur, phosphorus and oxygen. Preferred heteroaryls are 5- and 6-membered aromatic rings which contain from about 1 to about 3 heteroatoms. Examples of heteroaryl groups include, but are not limited to, pyridinyl, imidazolyl, pyrimidinyl, pyrazolyl, (1,2,3)- and (1,2,4)-triazolyl, pyrazinyl, tetrazolyl, furyl, thienyl, isoxazolyl, oxazolyl, pyrrolyl, thiazolyl, pyrrole, thiophenyl, furanyl, pyridazinyl, isothiazolyl, and S-triazinyl.

"N-heteroaryl" refers to monocyclic or bicyclic aromatic ring having at least one nitrogen atom in the aromatic ring moiety. Exemplary N-heteroaryls include, but are not limited to, pyridinyl, imidazolyl, pyrimidinyl, pyrazolyl, (1,2,3)- and (1,2,4)-triazolyl, pyrazinyl, tetrazolyl, isoxazolyl, oxazolyl, pyrrolyl, pyrrole, pyridazinyl, and isothiazolyl. Preferably, N-heteroaryl is pyridinyl. More preferably, N-heteroaryl is pyridin-3-yl.

The term "aryl containing at least one nitrogen substituent" refers to an aryl moiety having a substituent such as an amino, including mono-, di-, and tri-alkyl amino groups; amido; or $C_1$-$C_4$ alkyl groups having an amino or an amido substituent. Preferably, an "aryl containing at least one nitrogen substituent" is an aryl moiety having amino, amido or $C_1$-$C_2$ alkyl having an amino or amido substituent; more preferably amino, amido or C, alkyl having an amino or amido substituent; still more preferably an amino or amido substituent; and most preferably an amino substituent.

Unless otherwise specified, the term "aromatic group" refers to aryl and heteroaryl groups.

The terms "substituted," "substituted derivative" and "derivative" when used to describe a chemical moiety means that at least one hydrogen bound to the unsubstituted chemical moiety is replaced with a different atom or a chemical moiety. Examples of substituents include, but are not limited to, alkyl, halogen, nitro, cyano, heterocycle, aryl, heteroaryl, amino, amide, hydroxy, ester, ether, carboxylic acid, thiol, thioester, thioether, sulfoxide, sulfone, carbamate, peptidyl, $PO_3H_2$, and mixtures thereof.

The terms "compound of the present invention," "compound of this invention," "compound of the invention," "prenylation inhibitor of the present invention," "prenylation inhibitor of this invention," and "prenylation inhibitor of the invention" are used interchangeably to refer to the compounds and complexes disclosed herein, and to their pharmaceutically acceptable salts, solvates, hydrates, polymorphs, and clatherates thereof, and to crystalline and non-crystalline forms thereof.

Compounds useful in the present invention, typically show a percent inhibition of at least about 20%, more preferably at least about 35% and more preferably at least about 50% when they are at a concentration of 10 μM.

A therapeutic dosage can generally be from about 0.1 to about 1000 mg/day, and preferably from about 10 to about 100 mg/day, or from about 0.1 to about 50 mg/Kg of body weight per day and preferably from about 0.1 to about 20 mg/Kg of body weight per day and can be administered in several different dosage units. Higher dosages, on the order of about 2-fold to about 4-fold, may be required for oral administration. In another aspect, the therapeutic dosage can be sufficient to achieve blood levels of the therapeutic agent of between about 5 micromolar and about 10 micromolar.

Formulations for topical application to eyes can be isotonic, mildly hypotonic, or mildly hypertonic. The osmolalites of the formulations can be in the ranges of 200-400 or 250-350 mOsm/kg. Deviations beyond these ranges, for example to 150-450 may be tolerated. Osmolalities depend on the solute concentrations, higher concentrations of solute yielding higher osmolalities. Solutes which can be used include ionic salts, and nonionic polyhydric alcohols, for example. Specific solutes which can be used include glycerol, mannitol, sodium chloride, and potassium chloride. Physiological saline can be used in the formulations. A relatively neutral pH of between 6.5 and 7.5 can be used, although more basic or acidic formulations between 4 and 8 are acceptable. Preservatives may be included, such as benzalkonium chloride, chlorobutanol, thimerosal, phenylmercuric acetate, and phenylmercuric nitrate. Surfactants can also be included as part of the formulations. One such surfactant is Tween 80™. Other components which can be used include polyvinyl alcohol, povidone, hydroxypropyl methyl cellulose, poloxamers, carboxymethyl cellulose, hydroxyethyl cellulose, polyvinylpyrrolidone, polystyrene sulfonic acid, and distilled water. Such formulations are preferably sterile.

The data presented below detail the properties of a class of GGTase-I inhibitor. GGTI-DU40 is a potent inhibitor of GGTase-I with $K_i$ of <1 nM. Inhibition of GGTase-I by the compound was competitive with the protein substrate, which likely accounts for its high degree of specificity. GGTI-DU40 is a cell-active compound, as demonstrated by its ability to elicit mislocalization of a geranylgeranylated form of H-Ras expressed in cells and its ability to attenuate Rho-dependent rounding of MBA-231 cells. As such, GGTI-DU40 provides a novel inhibitor that will facilitate rational manipulation of GGTase-I mediated biologies and signaling processes in mammalian cells.

Mechanistically GGTI-DU40 competes for the CaaX peptide binding site on GGTase-I. In this property it is similar to several other described GGTIs, although structurally GGTI-DU40 is distinct from other inhibitors of the enzyme. The most obvious difference between GGTI-DU40 and the best-detailed GGTIs is that the latter are peptidomimetics and thus retain many features of the CaaX peptides (18-19, 40). The newest optimizations of these peptidomimetic inhibitors focused on removing the thiol contained within the cysteine residue mimic, leading to the generation of imidazole and pyridine substituted compounds (19). GGTI-DU40 has a similarity to these newer compounds due to its pyrazole located in a position similar to the imidazole found, for example, in GGTI-2147 (19). However, GGTI-DU40 has a nearly fully substituted pyrazole group (methylsulfanylethyl, dichlorobenzene, and a pyridine), whereas other GGTIs do not. These structural features hint at multiple interaction sites that participate in the high affinity interaction between GGTI-DU40 and GGTase-I.

One unexpected finding of our study was the preferential blockade of monomeric G protein signaling, via an impact on Rho, verus heterotrimeric G protein signaling, via an impact on Gβγ. One potential mechanism for the selective effects is the variable half-life/stabilities of different geranylgeranylated proteins. Further investigation of this property is warranted since selective blockade of specific geranylgeranylated proteins and signaling pathways could expand the utility of GGTase-I inhibitors as biological tools and in therapeutic applications.

The important role for geranylgeranlyated proteins such as Rho, in numerous diseases is increasingly being appreciated (41, 42, 36). In addition to potentially suppressing alternate prenylation of K-Ras, the impact of GGTI-DU40 on proteins such as RhoA/C and Cdc42 may prove to be beneficial in limiting oncogenesis by inhibiting proliferation and invasion (43, 44, 36). Rho activity has a clear function in angiogenesis (45), which in turn plays a critical role in the pathogenesis of tumors, rheumatoid arthritis, atherosclerosis, psoriasis, and diabetic retinopathy (46). In multiple sclerosis, leukocytes and monocytes infiltrate into the central nervous system as part of an inappropriate inflammatory response, and recent evidence suggests that this migration requires Rho signaling and that inhibition of prenylation can lead to decreased inflammatory disease progression (47, 48). As inflammation is thought to be involved in macular degeneration, the inhibitors of the present invention also are useful for inhibiting progression of macular degeneration. Additionally, replication of Hepatitis C virus can be attenuated by inhibiting GGTase-I, providing a new therapeutic prospect for this increasingly-prevalent disease (49, 50). Further experiments using GGTIs alone and in combination with FTIs and other first-line anti-cancer agents are necessary to evaluate the impact these agents could have on specific cancers and other pathologies; such studies will determine the appropriateness of where and when GGTIs should enter clinical trials. There is now a clear relationship between mechanism-based inhibition of CaaX motif processing and attenuation of tumor progression and other pathologies, and effective GGTIs will be indispensable in elucidating these processes while also providing the tools to test the hypothesis that inhibition of this enzyme could have therapeutic benefits.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Materials and Methods

Materials

Farnesyl diphosphate (FPP) and geranylgeranyl diphosphate (GGPP) were purchased from Biomol, Inc (Plymouth Meeting, Pa.). S-adenosine-L-methionine (AdoMet) was purchased from Sigma (St. Louis, Mo.). $^3$H-GGPP, $^3$H-FPP, and $^3$H-AdoMet were purchased from PerkinElmer (Boston, Mass.). Geneticin was purchased from Invitrogen (Carlsbad, Calif.). The FTI L-744,832 was purchased from EMD Biosciences (San Diego, Calif.). Streptavidin-Sepharose was purchased from Amersham Biosciences (Uppsla Sweden). Biotin-S-famsyl-L-cysteine was synthesized and purified as previously described (27). GGTI-DU40 and its inactive analog, SN-DU40, were synthesized by PPD Discovery (Research Triangle Park, N.C.) and by the Duke Small Molecule Synthesis Facility; the preparation of these compounds will be described elsewhere.

Enzyme Assays

FTase and GGTase-I activities were determined by following incorporation of radiolabeled isoprenoid from $^3$H-FPP and $^3$H-GGPP into Ras proteins as described previously (28). Briefly, purified mammalian FTase or GGTase-I (50 ng, expressed in Sf9 cells) (29, 30) were used to initiate reactions containing 0.5 µM FPP or GGPP, respectively and 1 µM of the appropriate purified His-tagged Ras substrates (H-Ras for FTase; Ras-CVLL for GGTase-I). Where indicated in the appropriate Figure legend, inhibitors were added at the indicated concentrations. Final DMSO concentration was 2% for all samples. Reactions were carried out for 10 min at 30° C. before precipitation and product determination. Kinetic assays in which GGPP concentration was varied employed 5 ng GGTase-I, and reactions were carried out for five min to prevent GGTase-I concentration from exceeding GGPP concentration.

GGTase-II activity was measured used bovine brain cytosol (200 µg protein) as the enzyme source and purified GST-tagged Rab5a as the protein substrate. The pGEX-Rab5a construct was a gift from Adrienne Cox (University of North Carolina). The assay was performed identically to that described above for the CaaX prenyltransferases except for the enzyme source and protein substrate and that the reaction time was increased to for 30 min.

Icmt assays were performed as described previously (27). Briefly, reactions were performed using biotin-S-farnsyl-L-cysteine (4 μM) as a substrate and $^3$H-AdoMet (5 μM, 7.5 Ci/mmol) as a methyl donor. Reactions were initiated by the addition of Sf9 membranes containing recombinant human Icmt (2 μg totoal protein) in the presence and absence of inhibitors. Reactions were carried out at room temperature for 20 min, and product formation determined.

Cell Culture and Microscopy

MDCK cells stably expressing GFP-H-Ras were a gift from Mark Philips (New York University School of Medicine). Ras-CVLL was cloned into pEGFP (Clontech) and used to transfect MDCK cells. Stable clones were then selected using both Geneticin and expression confirmed by analysis of GFP expression as visualized by fluorescence microscopy. MDCK cells were always cultured as a monolayer in DMEM with 10% FBS. For drug treatment experiments, cells were plated onto glass-bottom microwell dishes (MatTek Corp, Ashland, Mass.) and experiments initiated approximately 24 h after cells reached confluence. All compounds tested were dissolved in DMSO and added to cells at a final DMSO concentration of 0.02%.

For the experiments assessing thrombin effects on cell morphology, MDA-MB-231 cells were plated onto glass-bottom microwell dishes at 10-20% confluence and grown for 18-24 h in the presence of serum. Cells were then washed once with PBS and media replaced with serum-free media (DMEM) including indicated compounds and incubated an additional 24 h. Cells were then imaged, treated with thrombin (1 U/mL for 20 min), and imaged again.

Assessment of receptor independent cell rounding was accomplished using adenovirus expressing the activated mutant of Gα12, Gα12$_{QL}$ (31). MDA-MB-231 cells were plated onto glass-bottom microwell dishes at 60% confluence and grown for 18-24 h in the presence of serum. Cells were then washed once with PBS and media replaced with serum-free media (DMEM) including any indicated compounds and incubated 6 h before addition of recombinant adenovirus. Following an additional 12 h incubation, cells were imaged using brightfield and GFP fluorescence microscopy. Cell images were acquired using an Eclipse TE300 microscope (Nikon) using either an oil immersion lens at 600× (for fluorescence of MDCK cells) or a plan fluor lens at 200× (for MBA-321 cells) and a SPOT digital camera (Diagnostic Instruments, Sterling Heights, Mich.) employing SPOT RT 3.02 software.

Calcium Mobilization Studies

For the experiments assessing thrombin-induced calcium flux, MDA-MB-231 were plated on glass coverslips and treated similarly to that described for the thrombin rounding experiments. Calcium flux was measured 24 h after withdrawal of serum and addition of inhibitors using the calcium-sensitive dye Fura 2-AM (Molecular Probes Inc)(32). MDA-MB-231 cells were dye loaded for 1 h with 2.5 μM Fura-2 AM in Hanks balanced salt solution (HBSS, supplemented with 10 mM glucose and 0.1% BSA). After dye loading, the coverslips were placed in a temperature controlled recording chamber and superfused with Hanks solution. Cells were excited alternately at 340 and 380 nm and fluorescence emission at 510 nm was measured every four sec during the course of each experiment. After baseline recording for 2 min, thrombin (1 U/mL) was superfused into the bath chamber for 1 min (~20 mL), followed by washout. Data is presented after baseline subtraction to show thrombin dependent calcium flux. Fluorescence measurements were acquired using a DeltaScan Illumination System (Photon Technology International (PTI), South Brunswick, N.J.) running on FELIX 1.4 software.

Gβγ Membrane Partitioning

MDA-MB-231 cells were grown in 10 cm dishes and treated exactly as in the thrombin cell rounding assay. Following drug treatment in serum free media, cells were harvested and lysed using ice cold hypotonic lysis buffer (70 mM HEPES pH 7.4, 2 mM EDTA, 1 mM DTT, and protease inhibitors). Following sonication, the whole cell lysate (75 μg protein) was centrifuged at 100,000×g for 45 min. Both the supernatant (S100) and pellet (P100) fractions were processed on 4-20% SDS-polyacrylamide gels and proteins transferred to nitrocellulose membranes for immunoblot analysis.

RhoGDI-Rho Interaction Assay

The interaction of GST-RhoGDI with endogenous Rho was assessed by protein interaction experiments. RhoGDI was generated as a glutathione-S-transferase fusion protein using a construct provided by Gary Bokoch (Scripps). The GST-RhoGDI fusion protein was incubated with treated MDA-MB-231 cell lysates (prepared identically to Gβγ partitioning above) for 1 hr at 4° C. in a total volume of 200 μl. Glutathione-sepharose was added and the mixture rotated at 4° C. for 30 min after which the affinity matrix was pelleted and washed three times with 500 μl of incubation buffer (70 mM HEPES, pH 7.5, 2 mM EDTA, 1 mM DTT, 150 mM NaCl, 0.1% Tween, 100 μM GDP, 2 mM MgCl$_2$). Proteins retained on the matrix were solubilized in 2× Laemmli loading buffer and separated by electrophoresis on denaturing, 4-20% polyacrylamide gels. Proteins were transferred to nitrocellulose membranes for immunoblotting with an anti-RhoA antibody (Santa Cruz, sc-179).

Unprenylated Rap1 Analysis

To measure levels of unprenylated Rap1 in cells, whole cell lysates of MDA-MB-231 cells (prepared identically to Gβγ partitioning above, 75 ug) were mixed with Laemmli loading buffer and boiled. Samples were then separated by electrophoresis on denaturing 4-20% polyacrylamide gels and proteins transferred to nitrocellulose membranes for immunoblotting with antisera specific for the unprenylated form of Rap1 (Santa Cruz, sc-1482, goat). Sample loading was verified by reprobing blots with antisera for total Rap1 (Santa Cruz, sc-65, rabbit).

Miscellaneous Methods

Graphing and curve fitting were performed using Prism (GraphPad, San Diego Calif.). Substrate-velocity curves were fit to the Michaelis-Menten equation, while double-reciprocal plots were fit using linear regression. The K$_i$ for GGTI-DU40 was calculated using nonlinear regression and shared parameter curve fitting for all inhibitor concentrations, the velocity equation used was $v = V_{max}[S]/(K_m(1+([I]/K_i))+[S])$.

Example 2

Identification of GGTI-DU40, a Potent Inhibitor of GGTase-I

A diverse chemical library was screened for GGTase-I inhibitors using an in vitro assay, and a novel pyrazole-based inhibitor with an IC$_{50}$ of ~10 μM was discovered. Medicinal chemists at PPD Discovery (Research Triangle Park, N.C.) then optimized this structure for potency. The result of this optimization was a novel compound which we have dubbed GGTI-DU40 (FIG. 1A, N—[(S)-1-Carbamoyl-2-phenylethyl]-4-[2-(3,4-dichlorophenyl)-4-(2-methylsulfanylethyl)-5-pyridin-3-yl-2-H-pyrazol-3-yloxy]butyramide). The medicinal chemistry route to the refinement of this compound will be reported separately (J. P. Strachen et al, in preparation).

Example 3

Kinetic Analysis of GGTase-I Inhibition by GGTI-DU40

Figure 1B:
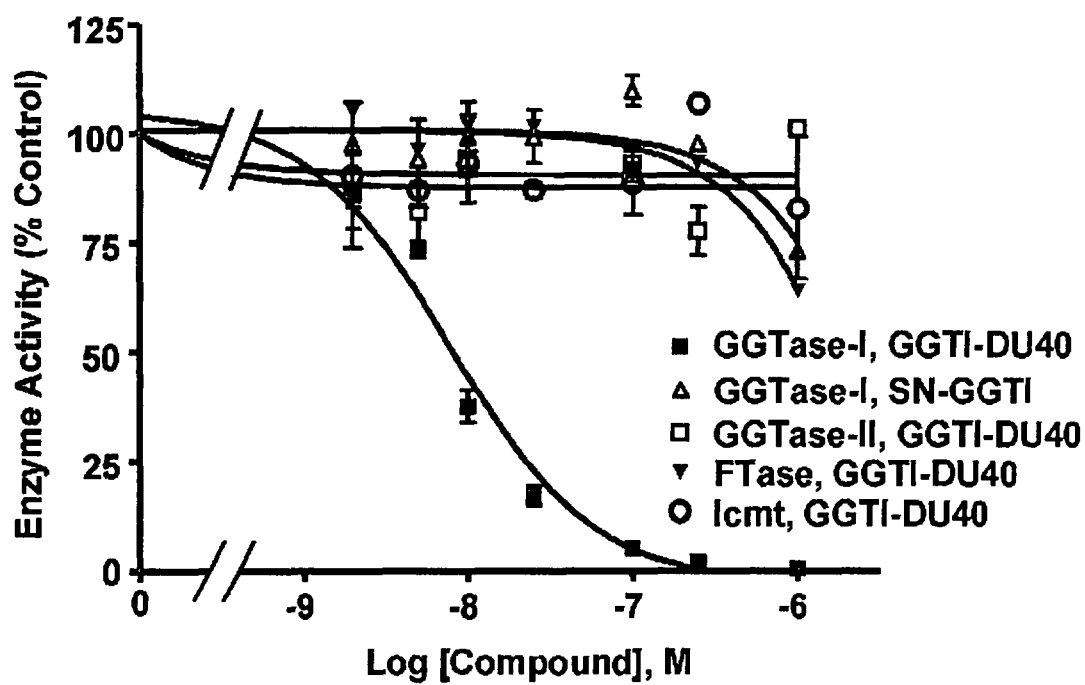

In an initial examination of the selectivity of GGTI-DU40, the ability of the compound to inhibit GGTase-I and other enzymes in the prenylation pathway was determined (FIG. 1B). GGTI-DU40 was a highly potent inhibitor of purified GGTase-I exhibiting an $IC_{50}$ of 8.24+/−0.97 nM. GGTI-DU40 inhibition of FTase was barely detectable in the concentration range tested, exhibiting an $IC_{50}$ for this closely-related enzyme of >2 μM, corresponding to a FTase/GGTase-I selectivity ratio of >250. GGTI-DU40 showed no detectable activity against GGTase-II (Rab geranylgeranyl-transferase) nor against Icmt methyltransferase (FIG. 1B). These data indicate GGTI-DU40 is a highly potent and selective inhibitor of GGTase-I. A structural analogue of GGTI-DU40, SN-DU40, that contains a single sulfur-to-nitrogen substitution (FIG. 1A), was also tested for GGTase-I inhibition. This single substitution resulted in a compound with an $IC_{50}$ of >2 μM for GGTase-I, providing a useful control for confirming mechanism-based effects of GGTI-DU40 in cells (see below).

Figure 2:
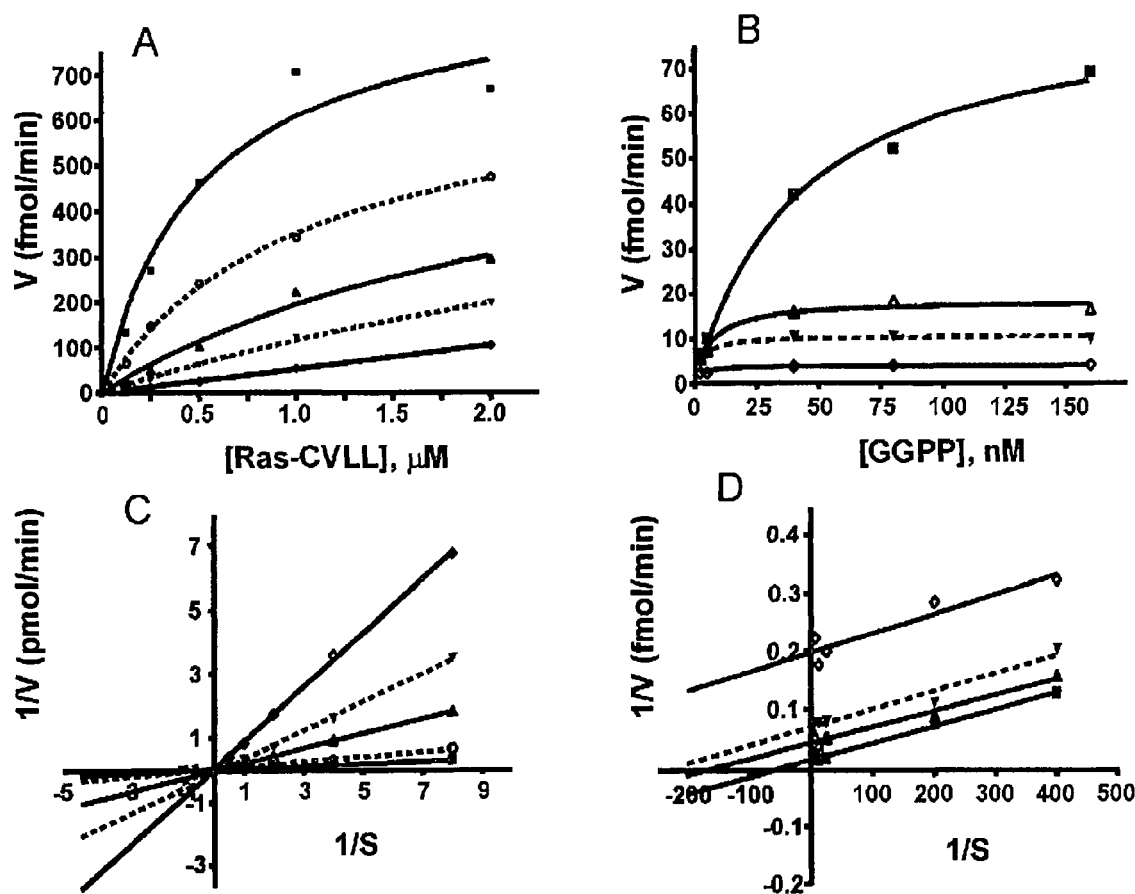
FIG. 2A-2D. Kinetic analysis of GGTI-DU40 inhibition of GGTase-I. Substrate-velocity curves for the inhibition of GGTase-I by GGTI-DU40 in the presence of fixed Ras-CVLL concentration (FIG. 2A) or fixed GGPP concentration (FIG. 2B) are shown.

GGTI-DU40 is of a distinct structural class than all other reported protein prenyltransferase inhibitors. Hence, it was considered important to understand the mechanism of GGTase-I inhibition by the compound. Accordingly, we undertook Michaelis-Menten-type analysis of the inhibition of GGTase-I. These kinetic data revealed that GGTI-DU40 is a competitive inhibitor with respect to the protein substrate (FIG. 2, panels A,C), and an uncompetitive inhibitor with respect to GGPP (FIG. 2, panels B,D). Hence, GGTI-DU40 competes for binding of the protein substrate, but not the isoprenoid substrate of GGTase-I. This feature likely contributes to this compound's high selectivity for GGTase-I. Analysis of the protein substrate competition data confirmed the high affinity of GGTI-DU40; the resultant calculated $K_i$ was of 0.78+/−0.10 nM. Given this high affinity, we tested GGTI-DU40 for potential time-dependent inhibition of GGTase-I, but no such behavior was observed (data not shown). These data establish GGTI-DU40 as a novel high affinity structure targeting the CaaX binding site of a protein prenyltransferase.

Example 4

Cellular Activity of GGTI-DU40

Figures 3A, 3B, 3C, 3D, 3E, 3F:
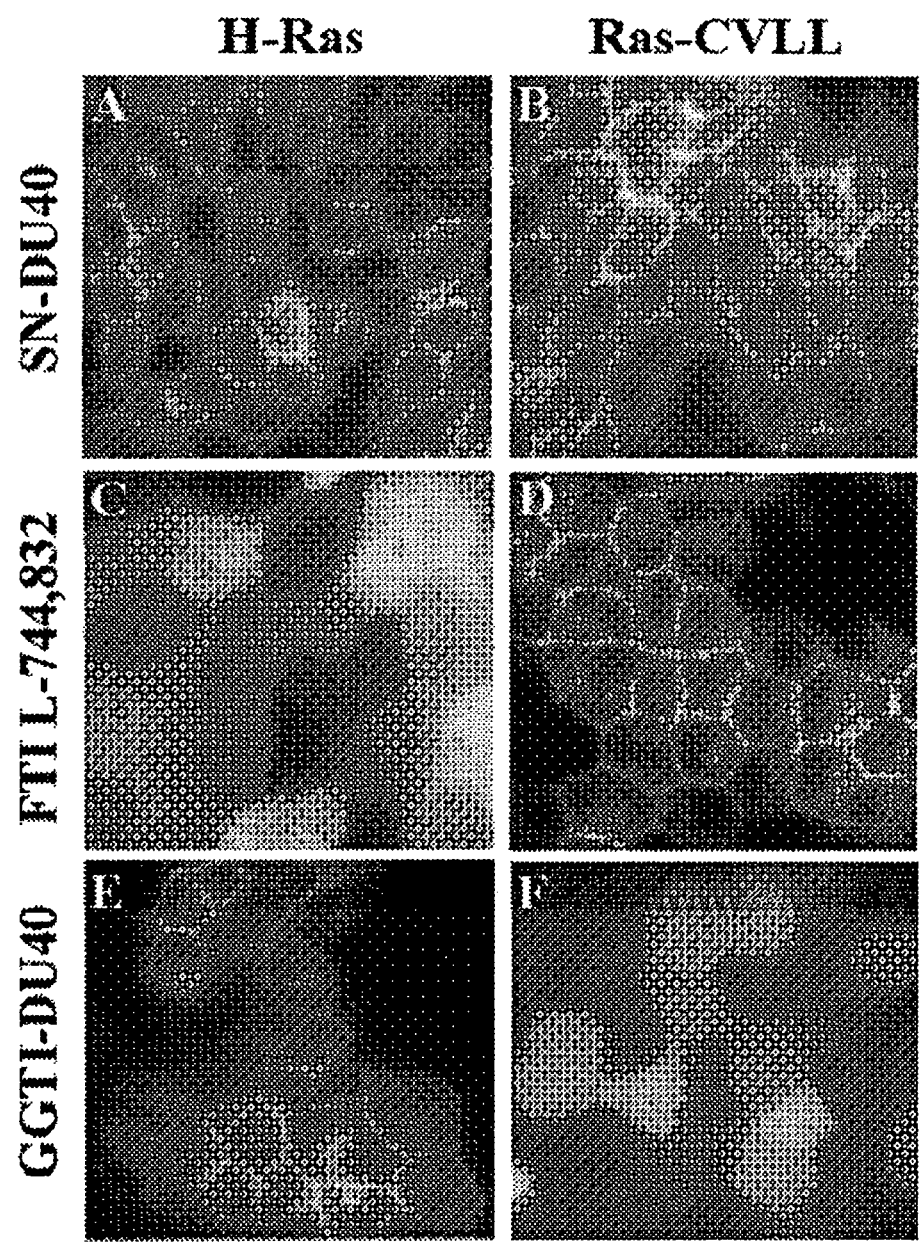
FIG. 3A-3F. GGTI-DU40 disrupts localization of geranylgeranylated Ras in MDCK cells. Depicted are fluorescence micrographs of MDCK cells stably expressing either GFP-H-Ras (FIG. 3A, 3C, 3E) or GFP-Ras-CVLL (FIG. 3B, 3D, 3F) treated with either SN-DU40 (20 μM, FIG. 3A, 3B), the FTI L-744,832 (20 μM, FIG. 3C, 3D), or GGTI-DU40 (20 μM, FIG. 3E, 3F) for 24 h. Visualization was performed as described in "Materials and Methods." Data shown are from a single experiment and is representative of at least three independent experiments for each condition.

Since GGTI-DU40 demonstrated favorable properties as a GGTase-I inhibitor in vitro, we explored its utility in targeting this enzyme in cells. An amenable system to evaluate the cellular effects of protein prenyltransferase inhibitors utilizes subcellular distribution of fluorescently-tagged fusions of Ras proteins. Wild type H-Ras normally localizes to the plasma membrane due to its ability to be modified by FTase, followed by processing by Rcel and Icmt, at its C-terminal sequence: CVLS. A variant of H-Ras, Ras-CVLL, contains a CaaX sequence terminating in Leu and thus its processing is initiated by geranylgeranylation by GGTase-I. In stably-transfected MDCK cells treated with either the vehicle DMSO (data not shown) or the inactive GGTI-DU40 analogue SN-DU40, both H-Ras and Ras-CVLL are predominantly localized to the plasma membrane (FIG. 3, panels A,B). Treatment with the FTI inhibitor L-744,832 (33) resulted in almost complete mislocalization of H-Ras (FIG. 3C), but no detectable mislocalization of Ras-CVLL was observed even at the highest concentration tested (20 μM, FIG. 3D) indicating the Ras-CVLL construct is exclusively geranylgeranylated in cells. On the other hand, treatment with GGTI-DU40 resulted in complete mislocalization of Ras-CVLL such that plasma membrane localized Ras was barely detectable (FIG. 3F), while this compound was without an effect on localization of H-Ras (FIG. 3E). Ras-CVLL mislocalization by GGTI-DU40 treatment could be detected at inhibitor concentrations as low as 2 μM (data not shown).

Example 5

Consequences of GGTI-DU40 Treatment on Cell Signaling

Figures 4A, 4B, 4C:
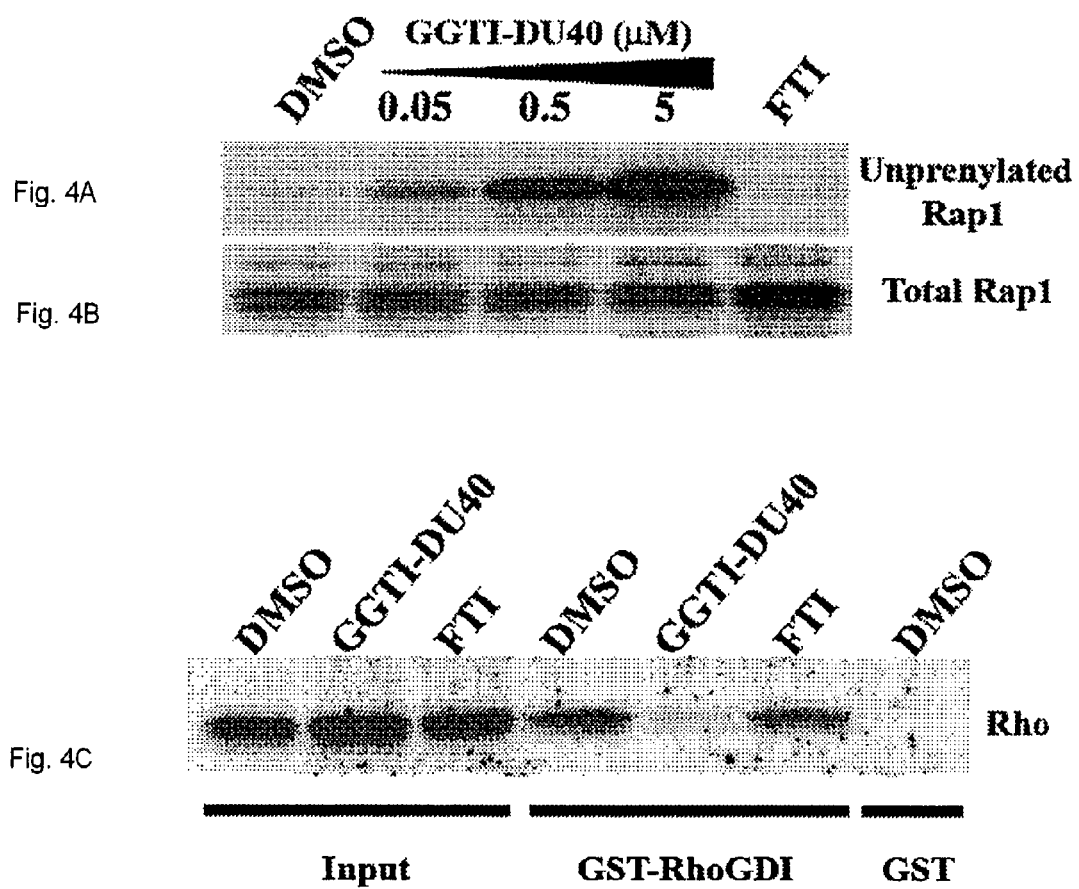
FIG. 4A-4C. GGTI-DU40 inhibits prenylation of Rap1 and Rho in MDA-MB-231 cells.

To further evaluate the effects of GGTase-I inhibition in cells, we chose the MDA-MB-231 adenocarcinoma cell line because its established biology (34, 35, 36). In initial studies, the ability of GGTI-DU40 treatment to impact the prenylation of a known geranylgeranylated protein was assessed using an antibody specific for the unprenylated form of Rap1. Upon GGTI-DU40 treatment of the MD-MBA-231 cells, a dose dependent increase in the level of unmodified Rap1 was observed (FIG. 4A). As expected, administration of FTI L-744,832 had no effect on Rap1 prenylation status. These data indicated the capacity of GGTI-DU40 to inhibit prenylation of endogenous proteins.

We next addressed whether GGTI administration could block normal functions of prenylated proteins. An attractive model here involves Rho GTPases. A major class of proteins that directly associate with Rho proteins in cells are termed RhoGDIs, and their binding to Rho GTPases is via an interaction that is known to be prenylation-dependent (37). Hence, we assessed the ability of GGTI-DU40 treatment of cells to impact on the ability of endogenous Rho proteins to bind RhoGDI. This interaction was directly measured in MDA-MB-231 cells using a GST-RhoGDI pull-down approach to assess the relative amount of endogenous Rho that was able to interact with RhoGDI after inhibitor treatment. As seen in FIG. 4B, a 24 h treatment of the cells GGTI-DU40 led to an almost complete loss in the ability of Rho proteins to associate with RhoGDI; this is precisely what would be expected if geranylgeranylation of Rho was blocked. In contrast, treatment of the cells with the FTI had no effect on the ability of Rho to interact with RhoGDI (FIG. 4B).

Figures 5A, 5B, 5C, 5D, 5E, 5F:
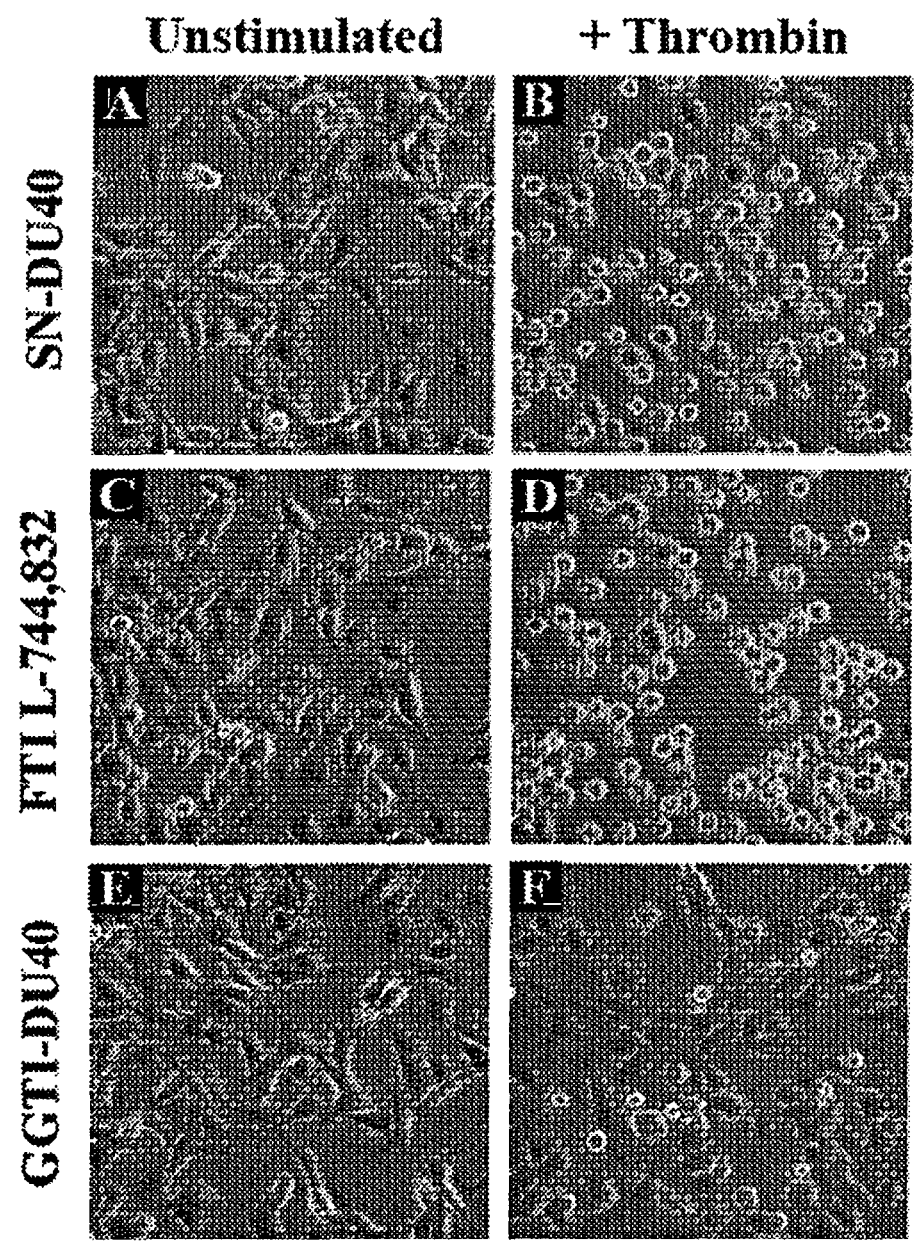
FIG. 5A-5F. GGTI-DU40 inhibits thrombin-induced cell rounding in MDA-MB-231 cells. Depicted are phase contrast micrographs of MDA-MB-231 cells before and after exposure to thrombin. Cells were pretreated with either SN-DU40 (20=μM, FIG. 5A, 5B), FTI (20=μM L-744,832, FIG. 5C, 5D), or GGTI-DU40 (5=μM, FIG. 5E, 5F) in serum starvation media for 24 h, imaged (Unstimulated), then treated with thrombin for 20 min before imaging again (+Thrombin). Data shown are from a single experiment and are representative of at least three independent experiments for each condition.

Signaling through the thrombin receptor in MDA-MB-231 cells results in a cell rounding phenotype that is principally mediated via the Rho GTPase (38, 35). In MDA-MB-231 cells treated with either the inactive analog SN-DU40 or the FTI, normal rounding in response to thrombin treatment was observed (FIG. 5). However, treatment of these cells with GGTI-DU40 dramatically inhibited thrombin-stimulated cell rounding (FIG. 5).

Although GGTase-I inhibition clearly impacted Rho function at the level of RhoGDI interaction (FIG. 4) and also Rho-mediated biology (thrombin-induced cell rounding; FIG. 5), there is clearly one other family of GGTase-I substrates that could have been important in the latter result. Specifically, Gγ subunits from heterotrimeric G-proteins are prenylated, and the majority are geranylgeranylated (39). To test the potential impact of GGTI-DU40 on Gγ subunits, membrane partitioning of Gβγ and calcium mobilization, the latter a downstream biology of thrombin receptor activation that is not dependent on Rho proteins, were determined in cells treated with GGTI-DU40. While GGTI treatment did elicit a partial loss of membrane-associated Gβγ (FIG. 6, upper panel), indicating a partial inhibition of Gγ prenylation, the majority of the Gβγ remained membrane-associated following this treatment. Furthermore, the ability of thrombin to elicit calcium mobilization following this GGTI treatment was unaffected (FIG. 6, lower panel), even though the same treatment conditions blocked thrombin's ability to stimulate cell rounding (FIG. 5). These data indicated that G protein coupling of the thrombin receptor is essentially unaffected by a 24 hr treatment of cells with the GGTI, and further point to an impact on Rho as being responsible for the cell rounding phenotype. In further support of this assessment, rounding of MDA-MB-231 cells elicited by expression of dominant-activate Gα12 (Gα12$_{QL}$), which directly engages the Rho axis without receptor involvement, was also blocked by GGTI-DU40 (Supplemental FIG. 1). Taken together, these data demonstrate a clear impact on function and signaling of Rho proteins by GGTase-I inhibition, and also indicate that it is possible to achieve a level of selectivity in inhibiting function of specific geranylgeranylated proteins in cells.

Inhibiting protein prenylation is an attractive means to modulate cellular processes controlled by a variety of signaling proteins, including oncogenic proteins like Ras and Rho GTPases. The largest class of prenylated proteins contain a so-called CaaX motif at their carboxy-termini and are subject to a maturation process initiated by attachment of an isoprenoid lipid by either protein farnesyltransferase (FTase) or protein geranylgeranyltransferase type I (GGTase-I). Inhibitors of FTase, termed FTIs, have been the subject of intensive development in the past decade and have shown efficacy in clinical trials. While GGTase-I inhibitors (GGTIs) have received less attention, accumulating evidence suggests GGTIs may augment therapies using FTIs and could be useful to treat a myriad of additional disease states. Here we describe the characterization of a selective, highly potent, and cell-active GGTase-I inhibitor, GGTI-DU40. Kinetic analysis revealed that inhibition by GGTI-DU40 is competitive with the protein substrate and uncompetitive with the isoprenoid substrate; the $K_i$ for the inhibition is 0.8 nM. GGTI-DU40 is highly selective for GGTase-I both in vitro and in living cells. Studies indicate GGTI-DU40 blocks prenylation of a number of geranylgeranylated CaaX proteins. Treatment of MDA-MB-231 breast cancer cells with GGTI-DU40 inhibited thrombin-induced cell rounding via a process that involves inhibition of Rho proteins without significantly effecting parallel mobilization of calcium via Gβγ. These studies establish GGTI-DU40 as a prime tool for interrogating biologies associated with protein geranylgeranylation and define a novel structure for this emerging class of experimental therapeutics.

Example 6

Inhibition of GGTI Increases Aqueous Humor Outflow in Perfused Porcine Eyes

Purpose: To determine the effects of inhibition of isoprenylation of small GTP-binding proteins such as Rho GTPases and the beta-gamma subunits of heterotrimeric G-proteins such as Galpha12/13 on aqueous humor outflow.

Methods: A selective inhibitor of GGTase-I (GGTI-DU40) was tested in this study to investigate its effects on actin cytosketal integrity, cell adhesions, cell-cell junctions, myosin II phosphorylation, and membrane localization of Rho, Rap and G-beta/gamma in trabecular meshwork (TM) cells, using immunofluorescence detection and immunoblotting analysis. The effects of GGTI-DU40 on aqueous humor outflow were determined using organ cultured, perfused anterior segments of porcine eyes.

The porcine TM primary cell cultures were treated with GGTI compounds in the presence of 10% serum for 6 hours and recorded for the changes in cell morphology (phase contrast microscope), actin cytoskeletal organization (phalloidin staining) and focal adhesions (vinculin staining).

Porcine primary TM cells were treated with GGTI compounds for 6 hours in the presence of 10% serum and the cell lysates were analyzed for the changes in myosin light chain (MLC) phosphorylation using phosphospecific-anti-MLC antibody.

GGTI-396586 was perfused in organ cultured anterior segments of enucleated porcine eyes at a constant flow at 37° C. Changes in aqueous humor outflow facility were determined. Values are expressed as percent change in outflow facility from baseline facility.

Figure 7:
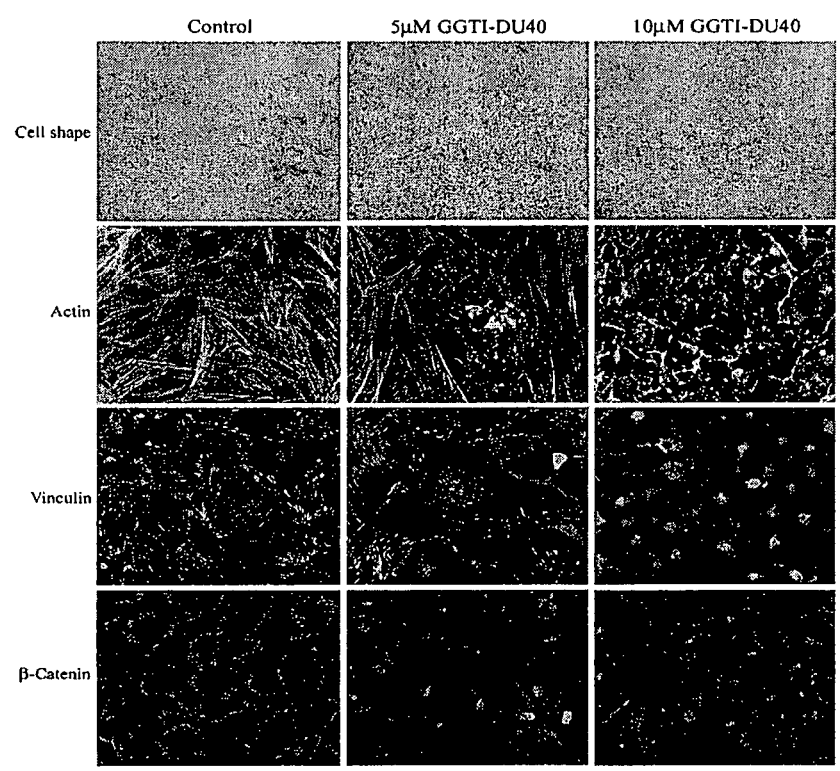
FIG. 7. GGTI-DU40-induced changes in porcine Trabecular meshwork cell shape, actin cytoskeletal organization, focal adhesions and cell-cell junctions. Two different concentrations were tested and found to have a dose-dependent response on the tested parameters.
Figures 8A, 8B:
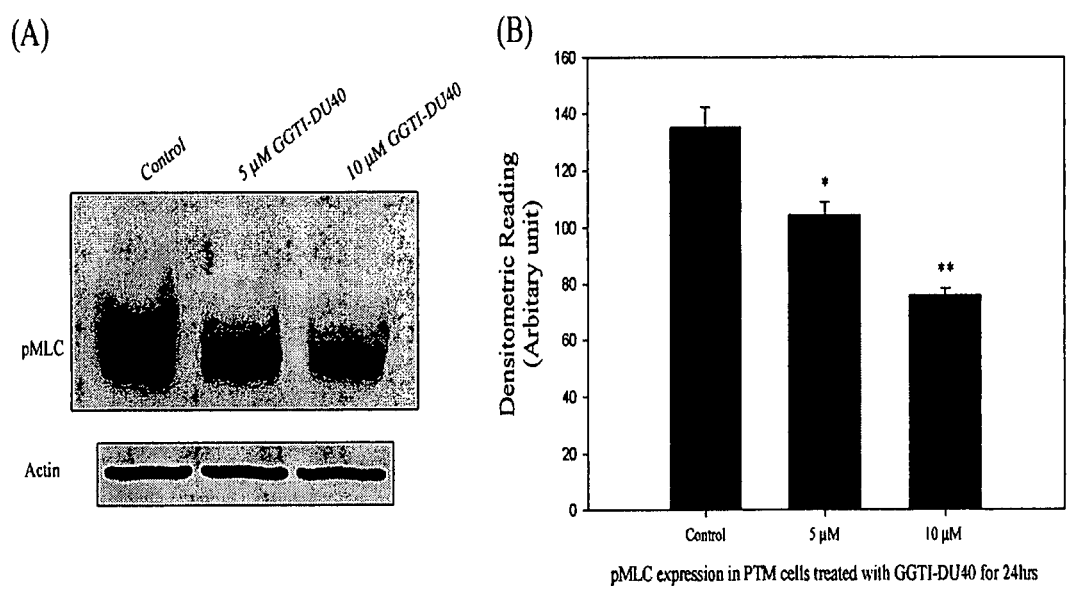
FIG. 8A-8B. GGTI-DU40-induced decrease in myosin light chain phosphorylation in porcine Trabecular meshwork cells. Myosin light chain phosphorylation was significantly reduced in GGTI-DU40 treated cells compared to untreated cells.
Figure 9:
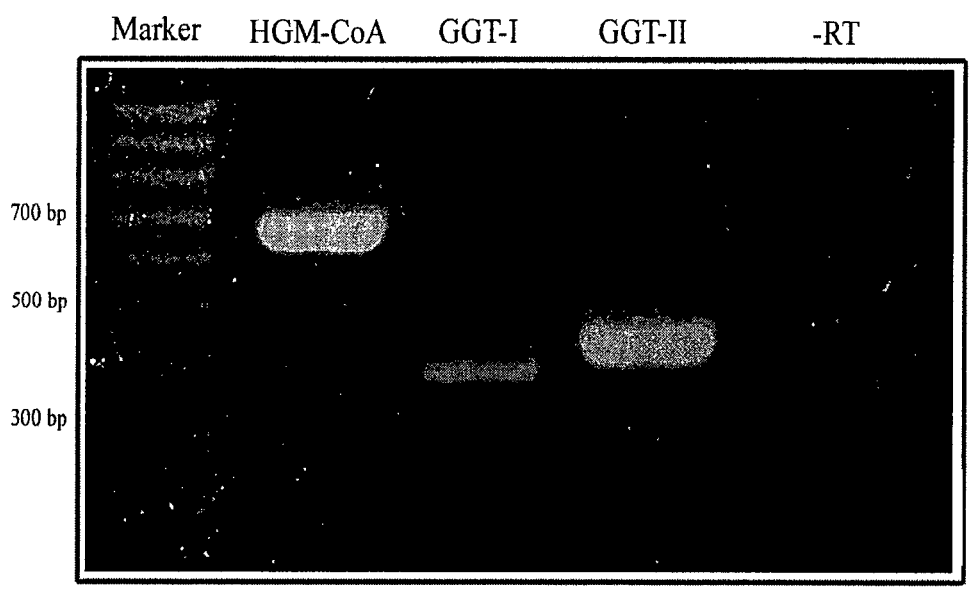
FIG. 9. Human Trabecular meshwork cells are confirmed to express the Geranylgeranyl transferases (I & II). RT-PCR analysis of total RNA derived from human trabecular meshwork cells demonstrated the expression of GGTI-1 and II.
Figure 10:
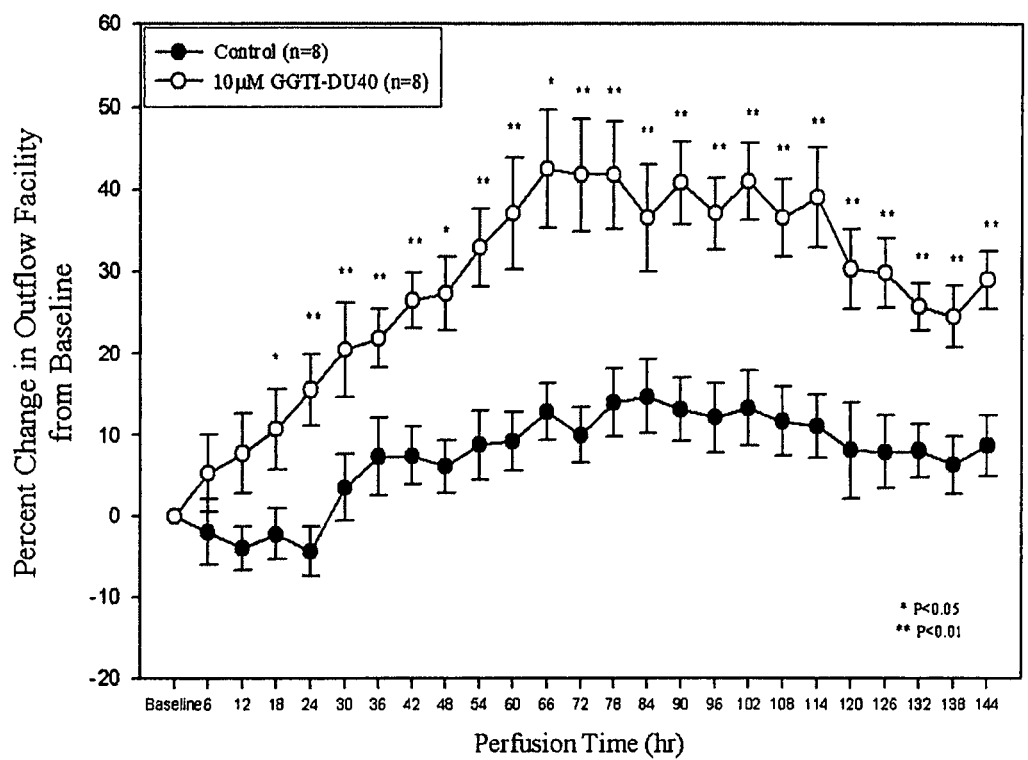
FIG. 10. Perfusion of GGTI-DU40 in organ cultured anterior segments of porcine eyes increases aqueous humor outflow facility. * indicates significant differences between control and drug perfused samples.
Figure 11:
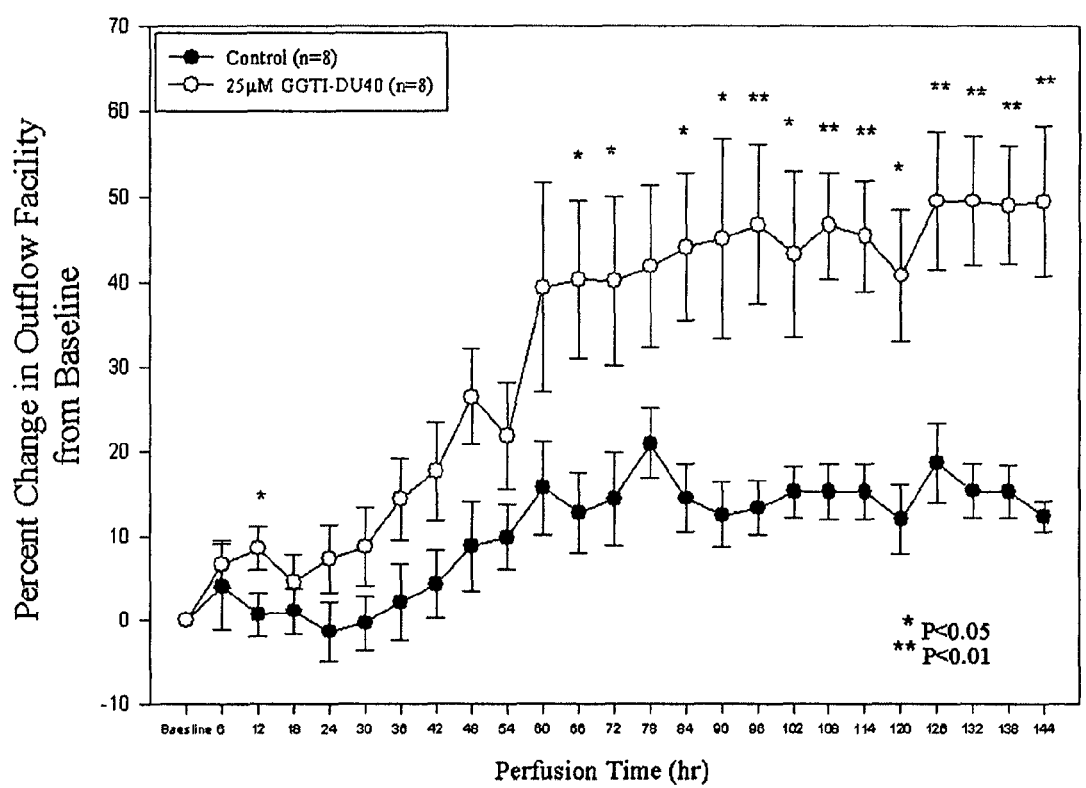
FIG. 11. GGTI-DU40-induced increase in aqueous humor outflow facility in organ cultured anterior segments of porcine eyes. * indicates significant differences between control and drug perfused samples.

Results: GGTI-DU40 treatment induced dose dependent (5 to 40 μM) changes in TM cell morphology, and caused reversible decreases in actin stress fibers and focal adhesions. See FIG. 7. Myosin light chain phosphorylation was decreased significantly (indicating relaxation of TM cells; see FIGS. 8A-8B), and membrane localization of Rho, Rap and G-beta/gamma was impaired in drug-treated TM cells. Aqueous outflow facility was increased significantly (by 30%) in eyes (n=8) perfused for 24 to 96 hours with 10 μM or 25 μM GGTI-DU40. See FIGS. 10 and 11, respectively.

Conclusions: These data demonstrate that inhibition of geranylgeranylation of Rho GTPases and heterotrimeric G-proteins in the aqueous outflow pathway increases aqueous humor outflow, possibly through the tissue relaxation, and through altered cell adhesive interactions and actin cytoskeletal organization in cells of the outflow pathway. This study indicates that the GGTase-I enzyme could serve as a potential molecular target for lowering increased ocular pressure in glaucoma patients.

REFERENCES

The disclosure of each reference cited is expressly incorporated herein.

1. Zhang, F. L., and Casey, P. J. (1996) *Annu Rev Biochem* 65, 241-269
2. Cox, A. D., and Der, C. J. (2002) *Curr Opin Pharmacol* 2, 388-393
3. Reid, T. S., Terry, K. L., Casey, P. J., and Beese, L. S. (2004) *J Mol Biol* 343, 417-433
4. Winter-Vann, A. M., and Casey, P. J. (2005) *Nat Rev Cancer* 5, 405-412
5. Casey, P. J., and Seabra, M. C. (1996) *J Biol Chem* 271, 5289-5292
6. Sebti, S. M., and Hamilton, A. D. (2000) *Expert Opin Investig Drugs* 9, 2767-2782
7. Boettner, B., and Van Aelst, L. (2002) *Gene* 286, 155-174
8. Levitzki, A. (1996) *Curr Opin Cell Biol* 8, 239-244
9. Einav, S., and Glenn, J. S. (2003) *J Antimicrob Chemother* 52, 883-886
10. Brown, M. S., Goldstein, J. L., Paris, K. J., Burnier, J. P., and Marsters, J. C., Jr. (1992) *Proc Natl Acad Sci USA* 89, 8313-8316
11. Karp, J. E., and Lancet, J. E. (2004) *Ann Hematol* 83 Suppl 1, S87-88
12. Doll, R. J., Kirschmeier, P., and Bishop, W. R. (2004) *Curr Opin Drug Discov Devel* 7, 478-486

13. Smith, V., Rowlands, M. G., Barrie, E., Workman, P., and Kelland, L. R. (2002) *Clin Cancer Res* 8, 2002-2009
14. Rao, S., Cunningham, D., de Gramont, A., Scheithauer, W., Smakal, M., Kourteva, G., Iveson, T., Andre, T., Dostalova, J., Illes, A., Belly, R., Perez-Ruixo, J. J., Park, Y. C., and Palmer, P. A. (2004) *J Clin Oncol* 22, 3950-3957
15. Rowell, C. A., Kowalczyk, J. J., Lewis, M. D., and Garcia, A. M. (1997) *J Biol Chem* 272, 14093-14097
16. Whyte, D. B., Kirschmeier, P., Hockenberry, T. N., Nunez-Oliva, I., James, L., Catino, J. J., Bishop, W. R., and Pai, J. K. (1997) *J Biol Chem* 272, 14459-14464
17. Fiordalisi, J. J., Johnson, R. L., 2nd, Weinbaum, C. A., Sakabe, K., Chen, Z., Casey, P. J., and Cox, A. D. (2003) *J Biol Chem* 278, 41718-41727
18. Lerner, E. C., Qian, Y., Hamilton, A. D., and Sebti, S. M. (1995) *J Biol Chem* 270, 26770-26773
19. Vasudevan, A., Qian, Y., Vogt, A., Blaskovich, M. A., Ohkanda, J., Sebti, S. M., and Hamilton, A. D. (1999) *J Med Chem* 42, 1333-1340
20. Carrico, D., Blaskovich, M. A., Bucher, C. J., Sebti, S. M., and Hamilton, A. D. (2005) *Bioorg Med Chem* 13, 677-688
21. Vogt, A., Sun, J., Qian, Y., Hamilton, A. D., and Sebti, S. M. (1997) *J Biol Chem* 272, 27224-27229
22. Sun, J., Qian, Y., Chen, Z., Marfirt, J., Hamilton, A. D., and Sebti, S. M. (1999) *J Biol Chem* 274, 6930-6934
23. Stark, W. W., Jr., Blaskovich, M. A., Johnson, B. A., Qian, Y., Vasudevan, A., Pitt, B., Hamilton, A. D., Sebti, S. M., and Davies, P. (1998) *Am J Physiol* 275, L55-63
24. Li, X., Liu, L., Tupper, J. C., Bannerman, D. D., Winn, R. K., Sebti, S. M., Hamilton, A. D., and Harlan, J. M. (2002) *J Biol Chem* 277, 15309-15316
25. Morgan, M. A., Wegner, J., Aydilek, E., Ganser, A., and Reuter, C. W. (2003) *Leukemia* 17, 1508-1520
26. Dan, H. C., Jiang, K., Coppola, D., Hamilton, A., Nicosia, S. V., Sebti, S. M., and Cheng, J. Q. (2004) *Oncogene* 23, 706-715
27. Baron, R. A., and Casey, P. J. (2004) *BMC Biochem* 5, 19
28. Thissen, J. A., and Casey, P. J. (1996) *Anal Biochem* 243, 80-85
29. Zhang, F. L., Diehl, R. E., Kohl, N. E., Gibbs, J. B., Giros, B., Casey, P. J., and Omer, C. A. (1994) *J Biol Chem* 269, 3175-3180
30. Zhang, F. L., Moomaw, J. F., and Casey, P. J. (1994) *J Biol Chem* 269, 23465-23470
31. Meigs, T. E., Fedor-Chaiken, M., Kaplan, D. D., Brackenbury, R., and Casey, P. J. (2002) *J Biol Chem* 277, 24594-24600
32. Grynkiewicz, G., Poenie, M., and Tsien, R. Y. (1985) *J Biol Chem* 260, 3440-3450
33. Sepp-Lorenzino, L., Ma, Z., Rands, E., Kohl, N. E., Gibbs, J. B., Oliff, A., and Rosen, N. (1995) *Cancer Res* 55, 5302-5309
34. Majumdar, M., Seasholtz, T. M., Buckmaster, C., Toksoz, D., and Brown, J. H. (1999) *J Biol Chem* 274, 26815-26821
35. Meigs, T. E., Juneja, J., DeMarco, C. T., Stemmle, L. N., Kaplan, D. D., and Casey, P. J. (2005) *J Biol Chem* 280, 18049-18055
36. Pille, J. Y., Denoyelle, C., Varet, J., Bertrand, J. R., Soria, J., Opolon, P., Lu, H., Pritchard, L. L., Vannier, J. P., Malvy, C., Soria, C., and Li, H. (2005) *Mol Ther* 11, 267-37.
37. Scheffzek, K., Stephan, I., Jensen, O. N., Illenberger, D., and Gierschik, P. (2000) *Nat Struct Biol* 7, 122-126
38. Jalink, K., and Moolenaar, W. H. (1992) *J Cell Biol* 118, 411-419
39. Schwindinger, W. F., and Robishaw, J. D. (2001) *Oncogene* 20, 1653-1660
40. Sun, J., Ohkanda, J., Coppola, D., Yin, H., Kothare, M., Busciglio, B., Hamilton, A. D., and Sebti, S. M. (2003) *Cancer Res* 63, 8922-8929
41. Sahai, E., and Marshall, C. J. (2002) *Nat Rev Cancer* 2, 133-142
42. Hall, A. (1998) *Science* 279, 509-514
43. Zohn, I. M., Campbell, S. L., Khosravi-Far, R., Rossman, K. L., and Der, C. J. (1998) *Oncogene* 17, 1415-1438
44. Aznar, S., Femandez-Valeron, P., Espina, C., and Lacal, J. C. (2004) *Cancer Lett* 206, 181-191
45. Park, H. J., Kong, D., Iruela-Arispe, L., Begley, U., Tang, D., and Galper, J. B. (2002) *Circ Res* 91, 143-150
46. Sivakumar, B., Harry, L. E., and Paleolog, E. M. (2004) *Jama* 292, 972-977
47. Walters, C. E., Pryce, G., Hankey, D. J., Sebti, S. M., Hamilton, A. D., Baker, D., Greenwood, J., and Adamson, P. (2002) *J Immunol* 168, 4087-4094
48. Greenwood, J., Walters, C. E., Pryce, G., Kanuga, N., Beraud, E., Baker, D., and Adamson, P. (2003) *Faseb J* 17, 905-907
49. Ye, J., Wang, C., Sumpter, R., Jr., Brown, M. S., Goldstein, J. L., and Gale, M., Jr. (2003) *Proc Natl Acad Sci USA* 100, 15865-15870
50. Wang, C., Gale, M., Jr., Keller, B. C., Huang, H., Brown, M. S., Goldstein, J. L., and Ye, J. (2005) *Mol Cell* 18, 425-434

We claim:

1. A method of treating glaucoma in a patient, comprising:
administering a selective inhibitor of geranylgeranyl transferase I (GGTI) to the patient, wherein the inhibitor competes with substrate protein for the CaaX peptide binding site on the GGTI, wherein the inhibitor inhibits geranylgeranyl transferase I at least 5 times more potently than farnesyl transferase, thereby increasing aqueous humor outflow through the trabecular meshwork pathway.

2. The method of claim 1 wherein the inhibitor of geranylgeranyl transferase is a cyclic acid anhydride comprising a lipid chain.

3. The method of claim 1 wherein the inhibitor is administered orally.

4. The method of claim 1 wherein the inhibitor is administered topically.

5. The method of claim 1 wherein the inhibitor is GGTI-286 having a structure

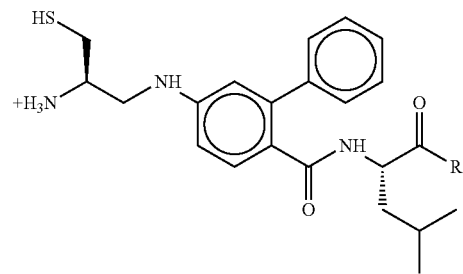

wherein R=OCH$_3$, or a pharmaceutically acceptable salt thereof.

6. The method of claim 1 wherein the inhibitor is GGTI-287 having a structure

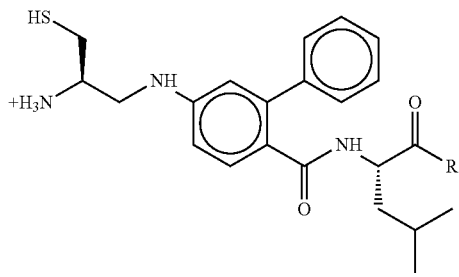

wherein R=O⁻, or a pharmaceutically acceptable salt thereof.

7. The method of claim 1 wherein the inhibitor is GGTI-297 having a structure

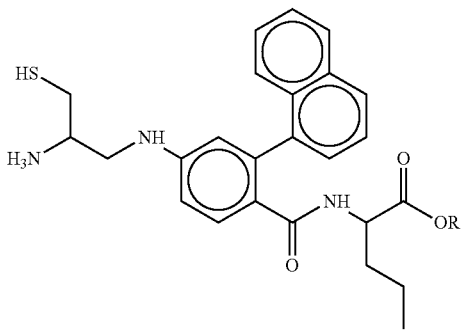

wherein R=H, or a pharmaceutically acceptable salt thereof.

8. The method of claim 1 wherein the inhibitor is GGTI-298 having a structure

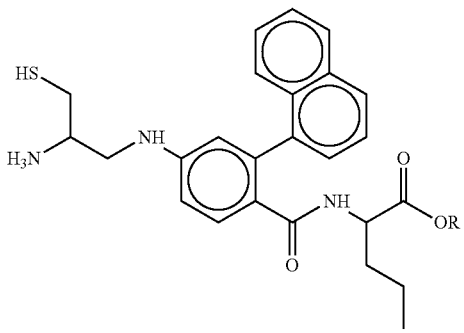

wherein R=CH₃, or a pharmaceutically acceptable salt thereof.

9. The method of claim 1 wherein the inhibitor is GGTI-2133 having a structure

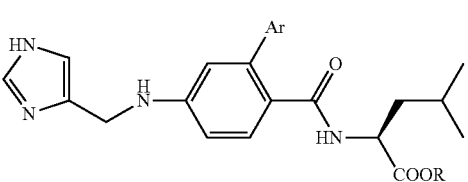

wherein R=H, and Ar=1-naphthyl, or a pharmaceutically acceptable salt thereof.

10. The method of claim 1 wherein the inhibitor is GGTI-2147 having a structure

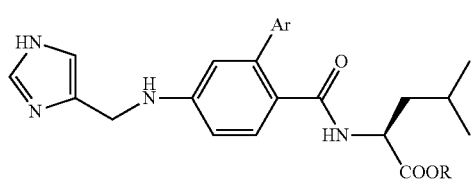

wherein R=CH₃, and Ar=1-naphthyl, or a pharmaceutically acceptable salt thereof.

11. The method of claim 1 wherein the inhibitor is GGTI-2166 having a structure

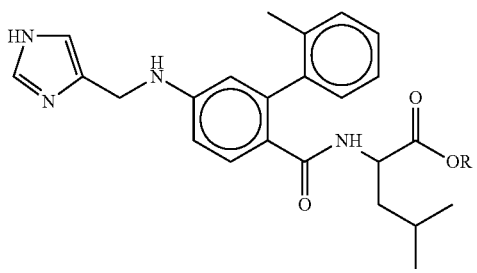

wherein R=CH₃, or a pharmaceutically acceptable salt thereof.

12. The method of claim 1 wherein the inhibitor is a compound of the following formula:

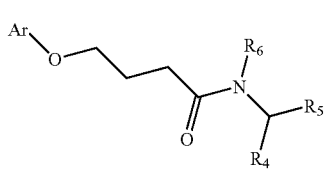

III wherein Ar is

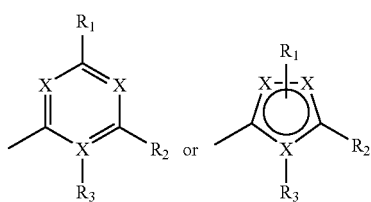

each X is independently C, N, O or S;
$R_1$ is phenyl, benzyl, methyl, ethyl, propyl, pyrimidine, 3,4-dimethylphenyl, 3-chloropyridazine, 2,4-dimethylpyrimidine, 3,4-difluorophenyl, 3,4-dichlorophenyl, 3,5-dichlorophenyl, $CH_2CF_3$, 4-trifluoromethylphenyl, 4-nitrophenyl, 4-bromophenyl, 3-bromophenyl, 4-methylphenyl, 4-methoxyphenyl, 4-chloro-2-methylphenyl, 4-fluorophenyl, 4-sulfonamidophenyl, 3-methoxyphenyl, 4-chlorophenyl, 3-chlorophenyl, 3,5-difluorophenyl, 4-aminophenyl, 1,3-dimethylpyrazole, ethanol, or 3,4-methylenedioxyphenyl;
$R_2$ is methyl, pyridine, pyridine-1-oxide, 3-cyanophenyl, 3-aminophenyl, 3-amidinophenyl, 3-dimethylaminophenyl, 2-methylthiazole, 4-methylthiadiazole, thiadiazole, 5-methylisoxazole, pyrazine, pyrimidine, 5-methylimidazole, 5-methylpyrazole, 2-benzylsulfanylpyridine, 6-benzylsulfanylpyridine, CH₂COOH, N(CH₃)₂, CH₂CH₂SCH₃ or CH₂-piperidinyl;

R₃ is absent, H, CH₂CH₂OH, CH₂CH₂OCH₃, CH₂CH₂N(CH₃)₂, CH₂CH₂NHCH₃, CH₂OH, (CH₂)₃OH, CH₂CH₂CO₂H, CH₂CO₂H, CH₂CH₂SOCH₃, CH₂CH₂SO₂CH—₃, CH₂CH₂SH or CH₂CH₂SCH₃;

R₄ is absent, H, NH₂, CON(CH₃)₂, CO₂H, CN, CH₂OH, CONH₂, CSNH₂, CONHOH, C(NH)NH₂, CONHNH₂, CONHCH₃, CH₂OCH₃, CONH-cyclohexyl, CO₂CH₃,

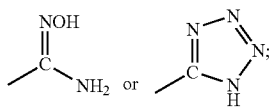

R₅ is absent, isopropyl, benzyl, 4-trifluoromethylbenzyl, 4-cyanobenzyl, 4-benzoylbenzyl, 3-chlorobenzyl, pentafluorobenzyl, 3,4-dichlorobenzyl, 2-fluorobenzyl, 4-methoxybenzyl, CH₂CH₂-phenyl, 4-fluorobenzyl, 4-phenylbenzyl, CH₂-imidazole, CH₂COOH, CH₂CH₂COOH, (CH₂)₄NH₂, CH₂CH₂SCH₃, 4-hydroxybenzyl, CH₂-naphthyl, 4-methylbenzyl, CH₂-indole, CH₂-thiophene, CH₂-cyclohexane, 4-chlorobenzyl, phenyl, ₂-hydroxybenzyl, 4-tertbutoxybenzyl, CH₂-benzylimidazole, 4-aminobenzyl, CH₂-pryid-3-yl, CH₂-pryid-2-yl, CH₂OH, (CH₂)₃NHC(NH)NH₂ or CH₂CH(CH₃)₂; and, R₆ is H, methyl, ethyl, propyl, isopropyl, CH₂CO₂H, CH₂CO₂Et, benzyl, or CH₂-(2-methoxynaphthyl); or, R₅ and R₆ together form:

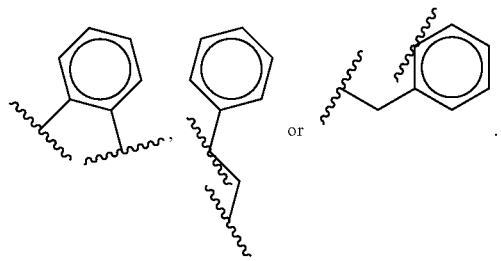

13. The method of claim 1 wherein the inhibitor is GGTI-396586 (GGTI-DU40; N—[(S)-1-Carbamoyl-2-pheylethyl]-4-[2-(3,4-diclolorophenyl)-4-(2-methylsulfanylethyl)-5-pyridin-3-yl-2-H-pyrazol-3-yloxy]butyramide) or a pharmaceutically acceptable salt thereof.

14. The method of claim 1 wherein the inhibitor inhibits geranylgeranyl transferase I at least 250 times more potently than farnesyl transferase.

15. The method of claim 1 wherein the inhibitor inhibits geranylgeranyl transferase I at least 10 times more potently than farnesyl transferase.

16. The method of claim 1 wherein the inhibitor inhibits geranylgeranyl transferase I at least 20 times more potently than farnesyl transferase.

17. The method of claim 1 wherein the inhibitor inhibits geranylgeranyl transferase I at least 25 times more potently than farnesyl transferase.

18. The method of claim 1 wherein the inhibitor inhibits geranylgeranyl transferase I at least 35 times more potently than farnesyl transferase.

19. The method of claim 1 wherein the inhibitor inhibits geranylgeranyl transferase I at least 45 times more potently than farnesyl transferase.

20. The method of claim 1 wherein the inhibitor inhibits geranylgeranyl transferase I at least 50 times more potently than farnesyl transferase.

21. The method of claim 1 wherein adenosine triphosphate is administered with or prior to the inhibitor.

22. The method of claim 1 wherein the inhibitor inhibits geranylgeranyl transferase I with a $K_i$<1 nM.

23. The method of claim 1 wherein the inhibitor is GGTI-DU40 (N—[(S)-1-Carbamoyl-2-phenylethyl]-4-[2-(3,4-dichlorophenyl)-4-(2-methylsulfanylethyl)-5-pyridin-3-yl-2-H-pyrazol-3-yloxy]butyramide, FW=612.58).

24. The method of claim 3 wherein the inhibitor is GGTI-DU40 (N—[(S)-1-Carbamoyl-2-phenylethyl]-4-[2-(3,4-dichlorophenyl)-4-(2-methylsulfanylethyl)-5-pyridin-3-yl-2-H-pyrazol-3-yloxy]butyramide, FW=612.58).

25. The method of claim 4 wherein the inhibitor is GGTI-DU40 (N—[(S)-1-Carbamoyl-2-phenylethyl]-4-[2-(3,4-dichlorophenyl)-4-(2-methylsulfanylethyl)-5-pyridin-3-yl-2-H-pyrazol-3-yloxy]butyramide, FW=612.58).

26. The method of claim 21 wherein the inhibitor is GGTI-DU40 (N—[(S)-1-Carbamoyl-2-phenylethyl]-4-[2-(3,4-dichlorophenyl)-4-(2-methylsulfanylethyl)-5-pyridin-3-yl-2-H-pyrazol-3-yloxy]butyramide, FW=612.58).

* * * * *